(12) United States Patent
Phillips et al.

(10) Patent No.: US 10,092,036 B2
(45) Date of Patent: Oct. 9, 2018

(54) AEROSOL DELIVERY DEVICE INCLUDING A HOUSING AND A COUPLER

(71) Applicant: R.J. REYNOLDS TOBACCO COMPANY, Winston-Salem, NC (US)

(72) Inventors: Percy D. Phillips, Pfafftown, NC (US); Michael F. Davis, Clemmons, NC (US); Nicholas H. Watson, Westfield, NC (US); Noah M. Minskoff, Palo Alto, CA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 301 days.

(21) Appl. No.: 14/981,051

(22) Filed: Dec. 28, 2015

(65) Prior Publication Data

US 2017/0181471 A1 Jun. 29, 2017

(51) Int. Cl.
*A61L 9/03* (2006.01)
*A24F 47/00* (2006.01)
(Continued)

(52) U.S. Cl.
CPC ............ *A24F 47/008* (2013.01); *A24F 15/12* (2013.01); *A61M 11/042* (2014.02);
(Continued)

(58) Field of Classification Search
None
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

N. Yati et al.; Abstract: *Sterilization using 365 nm UV-LED*; Conf. Proc. IEEE Eng. Med. Biol. Soc.; 2007 (1 page) Downloaded from website on Aug. 21, 2014 http://www.ncbi.nlm.nih.gov/pubmed/18003342.

(Continued)

*Primary Examiner* — Thor Campbell
(74) *Attorney, Agent, or Firm* — Womble Bond Dickinson (US) LLP

(57) ABSTRACT

The present disclosure relates to aerosol delivery devices. The aerosol delivery devices may include a control body and a cartridge including an atomizer and a reservoir configured to contain an aerosol precursor composition. The control body may include a housing defining an electrical power source cavity that extends along a first longitudinal axis and is configured to receive an electrical power source. The control body may additionally include a coupler configured to engage a cartridge including an aerosol precursor composition such that the cartridge extends along a second longitudinal axis. The first longitudinal axis and the second longitudinal axis may be non-coaxial and oriented substantially parallel to one another. A related assembly method is also provided.

19 Claims, 24 Drawing Sheets

(51) Int. Cl.
  *H02J 7/00* (2006.01)
  *A24F 15/12* (2006.01)
  *A61M 15/06* (2006.01)
  *A61M 11/04* (2006.01)
  *A61M 16/00* (2006.01)

(52) U.S. Cl.
  CPC ........... *A61M 15/06* (2013.01); *H02J 7/0029* (2013.01); *A61M 2016/0018* (2013.01); *A61M 2205/13* (2013.01); *A61M 2205/276* (2013.01); *A61M 2205/332* (2013.01); *A61M 2205/502* (2013.01); *A61M 2205/583* (2013.01); *A61M 2205/584* (2013.01); *A61M 2205/586* (2013.01); *A61M 2205/587* (2013.01); *A61M 2205/60* (2013.01); *A61M 2205/8206* (2013.01); *A61M 2205/8262* (2013.01); *H02J 2007/0037* (2013.01)

(56) References Cited

U.S. PATENT DOCUMENTS

| | | | |
|---|---|---|---|
| 2,104,266 A | 1/1938 | McCormick | |
| 3,200,819 A | 8/1965 | Gilbert | |
| 4,284,089 A | 8/1981 | Ray | |
| 4,303,083 A | 12/1981 | Burruss, Jr. | |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen et al. | |
| 5,388,594 A * | 2/1995 | Counts ................... | A24F 47/008 128/202.21 |
| 5,408,574 A | 4/1995 | Deevi et al. | |
| 5,468,936 A | 11/1995 | Deevi et al. | |
| 5,498,850 A | 3/1996 | Das | |
| 5,505,214 A * | 4/1996 | Collins ................... | A24F 47/008 128/202.21 |
| 5,515,842 A | 5/1996 | Ramseyer | |
| 5,530,225 A | 6/1996 | Hajaligol | |
| 5,564,442 A * | 10/1996 | MacDonald ............ | A24F 13/00 131/194 |
| 5,591,368 A * | 1/1997 | Fleischhauer ......... | A24F 47/008 131/194 |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiling et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,803,550 B2 * | 10/2004 | Sharpe ................... | H05B 6/105 219/263 |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 | 3/2011 | Hamano et al. | |
| 8,127,772 B2 | 3/2012 | Montaser | |
| 8,314,591 B2 | 11/2012 | Terry et al. | |
| 8,365,742 B2 | 2/2013 | Hon | |
| 8,371,310 B2 * | 2/2013 | Brenneise ............. | A24F 47/008 131/194 |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,757,147 B2 | 6/2014 | Terry et al. | |
| 9,468,234 B2 * | 10/2016 | Fernando .............. | A24F 47/008 |
| 9,497,999 B2 * | 11/2016 | Lord ..................... | A24F 47/008 |
| 9,532,605 B2 * | 1/2017 | Yamada ................ | A24F 47/008 |
| 9,603,386 B2 * | 3/2017 | Xiang ................... | A24F 47/008 |
| 9,603,388 B2 * | 3/2017 | Fernando ............. | A24F 47/008 |
| 2002/0146242 A1 | 10/2002 | Vieira | |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2005/0268911 A1 | 12/2005 | Cross et al. | |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 | 9/2010 | Hearn | |
| 2010/0242974 A1 | 9/2010 | Pan | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0094523 A1 | 4/2011 | Thorens et al. | |
| 2011/0126848 A1 | 6/2011 | Zuber et al. | |

(56) References Cited

U.S. PATENT DOCUMENTS

| | | |
|---|---|---|
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0255546 A1 | 10/2012 | Goetz et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1* | 1/2014 | Sebastian ............ A24F 47/008 131/328 |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0202454 A1 | 7/2014 | Buchberger |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0034103 A1 | 2/2015 | Hon |
| 2015/0053217 A1 | 2/2015 | Steingraber et al. |
| 2015/0101625 A1* | 4/2015 | Newton ............ A24F 47/008 131/329 |
| 2015/0181942 A1* | 7/2015 | Holzherr ............ A24F 47/008 131/328 |
| 2016/0262459 A1* | 9/2016 | Monsees ............ A61M 11/042 |
| 2016/0302488 A1* | 10/2016 | Fernando ............ A24F 47/008 |

FOREIGN PATENT DOCUMENTS

| | | |
|---|---|---|
| CA | 2 947 135 | 11/2015 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 02/47499 | 6/2002 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2012/114322 | 8/2012 |
| WO | WO 2013/089551 | 6/2013 |
| WO | WO 2013/102612 | 7/2013 |
| WO | 2015/140555 | 9/2015 |
| WO | WO 2015/149332 | 10/2015 |

OTHER PUBLICATIONS

Richard Halliday; *Key Benefits of Next-Gen UV LED Technology*; Lumex® (4 pages) Downloaded from website on Aug. 21, 2014; http://www.digikey.com/Web%20Export/Supplier%20Content/Lumex_67/PDF/Lumex_UV_LEDs_TechNotes.pdf?redirected=1.

Olga Bilenko et al.; SETi Sensor Electronic Technology, Inc.; *Water Sterilization Using Semiconductor-Based Deep Ultraviolet Light Sources* ( 2 pages) Downloaded from website on Aug. 21, 2014 http://www.s-et.com/water-sterilization-using-uv-leds.pdf.

Interntional Search Report issued in corresponding International Patent Application PCT/IB2016/058021 filed Dec. 27, 2016.

\* cited by examiner

PROVIDE A HOUSING DEFINING AN ELECTRICAL POWER SOURCE CAVITY CONFIGURED TO RECEIVE AN ELECTRICAL POWER SOURCE AND A CARTRIDGE CAVITY CONFIGURED TO RECEIVE A CARTRIDGE INCLUDING AN AEROSOL PRECURSOR COMPOSITION — 402

POSITION AN ELECTRICAL CONTACT IN THE ELECTRICAL POWER SOURCE CAVITY, THE ELECTRICAL CONTACT BEING CONFIGURED TO ENGAGE THE ELECTRICAL POWER SOURCE — 404

POSITION A COUPLER IN THE CARTRIDGE CAVITY, THE COUPLER BEING CONFIGURED TO ENGAGE THE CARTRIDGE — 406

FIG. 16

AEROSOL DELIVERY DEVICE INCLUDING A HOUSING AND A COUPLER

FIELD OF THE DISCLOSURE

The present disclosure relates to aerosol delivery devices, and more particularly, to aerosol delivery devices that include a housing and a coupler. The aerosol delivery device may include an atomizer comprising a heating element configured to heat an aerosol precursor. The aerosol precursor composition, which may include components made or derived from tobacco or otherwise incorporate tobacco, is heated by the atomizer to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. App. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

Certain existing embodiments of aerosol delivery devices include a control body and a cartridge. A power source (e.g., a battery) may be positioned in the control body and an aerosol precursor composition may be positioned in the cartridge. The cartridge and the control body may engage one another to define an elongated tubular configuration. However, certain other form factors for aerosol delivery devices may be desirable.

BRIEF SUMMARY OF THE DISCLOSURE

The present disclosure relates to aerosol delivery devices which, in certain embodiments, may be characterized as electronic cigarettes. In one aspect an aerosol delivery device is provided. The aerosol delivery device may include a housing. The housing may define an electrical power source cavity configured to receive an electrical power source, and a cartridge cavity configured to receive a cartridge including an aerosol precursor composition. The electrical power source cavity and the cartridge cavity may be elongated and respectively define a longitudinal axis. The longitudinal axis of the electrical power source cavity and the longitudinal axis of the cartridge cavity may be non-coaxial and oriented substantially parallel to one another.

In some embodiments the aerosol delivery device may further include the electrical power source. Additionally, the aerosol delivery device may include the cartridge. Further, the aerosol delivery device may include a coupler positioned within the housing and configured to engage the cartridge. The aerosol delivery device may additionally include an outer cover engaged with an exterior of the housing.

In some embodiments the housing may further define a viewing opening at the cartridge cavity. Additionally, the aerosol delivery device may include an illumination source configured to illuminate the cartridge in the cartridge cavity. The aerosol delivery device may further include an electronic display. The housing may include an access door configured to provide access to the electrical power source cavity. The housing may define an external opening at the cartridge cavity configured to receive the cartridge therethrough. The housing may define a dividing wall that separates the electrical power source cavity from the cartridge cavity.

In an additional aspect a method for assembling an aerosol delivery device is provided. The method may include providing a housing. The housing may define an electrical power source cavity configured to receive an electrical power source and a cartridge cavity configured to receive a cartridge including an aerosol precursor composition. The electrical power source cavity and the cartridge cavity may be elongated and respectively define a longitudinal axis. The longitudinal axis of the electrical power source cavity and the longitudinal axis of the cartridge cavity may be non-coaxial and oriented substantially parallel to one another. Further, the method may include positioning an electrical contact in the electrical power source cavity. The electrical contact may be configured to engage the electrical power source. Additionally, the method may include positioning a coupler in the cartridge cavity. The coupler may be configured to engage the cartridge.

In some embodiments the method may further include inserting the electrical power source in the electrical power source cavity and engaging the electrical power source with the electrical contact. Additionally, the method may include inserting the cartridge into the cartridge cavity and engaging the cartridge with the coupler. Inserting the cartridge into the cartridge cavity may include inserting the cartridge through an external opening defined by the housing.

In some embodiments providing the housing may include defining a viewing opening at the cartridge cavity. Further, the method may include engaging an outer cover with an exterior of the housing. The method may additionally include positioning an illumination source in the housing. The illumination source may be configured to illuminate the cartridge in the cartridge cavity. In some embodiments the method may additionally include engaging an electronic display with the housing. Providing the housing may include engaging a first body portion with a second body portion. Providing the housing further may further include engaging an access door with at least one of the first body portion and the second body portion. The access door may be configured to selectively provide access to the electrical power source cavity.

In an additional aspect an aerosol delivery device is provided. The aerosol delivery device may include a housing defining an electrical power source cavity configured to receive an electrical power source. The electrical power source cavity may define a first longitudinal axis. The aerosol delivery device may additionally include a coupler engaged with the housing and configured to engage a cartridge including an aerosol precursor composition such that the cartridge extends along a second longitudinal axis. The first longitudinal axis and the second longitudinal axis may be non-coaxial and oriented substantially parallel to one another.

In some embodiments the aerosol delivery device may further include the electrical power source. Additionally, the aerosol delivery device may include a controller. The controller may be wrapped at least partially about the electrical power source.

In some embodiments the aerosol delivery device may further include the cartridge. The cartridge may include a viewing window. The aerosol delivery device may additionally include an illumination source configured to direct illumination through the viewing window.

In some embodiments the housing may include a coupler portion. The coupler may be positioned at least partially within the coupler portion. The housing may include a button assembly. The button assembly may be configured to control a power output level directed from the electrical power source to the cartridge. The button assembly may at least partially define a dividing wall that separates the cartridge from the electrical power source cavity. Further, the aerosol delivery device may include an illumination source. The button assembly may include an illumination source cover configured to direct illumination produced by the illumination source therethrough.

In an additional aspect a method for assembling an aerosol delivery device is provided. The method may include providing a housing defining an electrical power source cavity configured to receive an electrical power source. The electrical power source cavity may define a first longitudinal axis. The method may additionally include engaging a coupler configured to engage a cartridge including an aerosol precursor composition with the housing such that the cartridge extends along a second longitudinal axis. The first longitudinal axis and the second longitudinal axis may be non-coaxial and oriented substantially parallel to one another. Further, the method may include positioning a controller in the housing. The controller may be configured to engage the electrical power source.

In some embodiments the method may further include engaging the electrical power source with the controller. Additionally, the method may include inserting the electrical power source in the electrical power source cavity simultaneously with positioning the controller in the housing. Further, the method may include engaging the cartridge with the coupler. The cartridge may include a viewing window. Further, the method may include positioning an illumination source in the housing. The illumination source may be configured to direct illumination through the viewing window.

In some embodiments providing the housing may include engaging a first body portion with a second body portion. Further, providing the housing further may include engaging an access door with at least one of the first body portion and the second body portion. The access door may be configured to block access to the electrical power source cavity. Providing the housing may further include engaging a button assembly with at least one of the first body portion and the second body portion. The method may additionally include positioning an illumination source in the housing and engaging an illumination source cover with the button assembly.

The illumination source cover may be configured to direct illumination produced by the illumination source therethrough.

These and other features, aspects, and advantages of the disclosure will be apparent from a reading of the following detailed description together with the accompanying drawings, which are briefly described below.

BRIEF DESCRIPTION OF THE FIGURES

Figure 1:
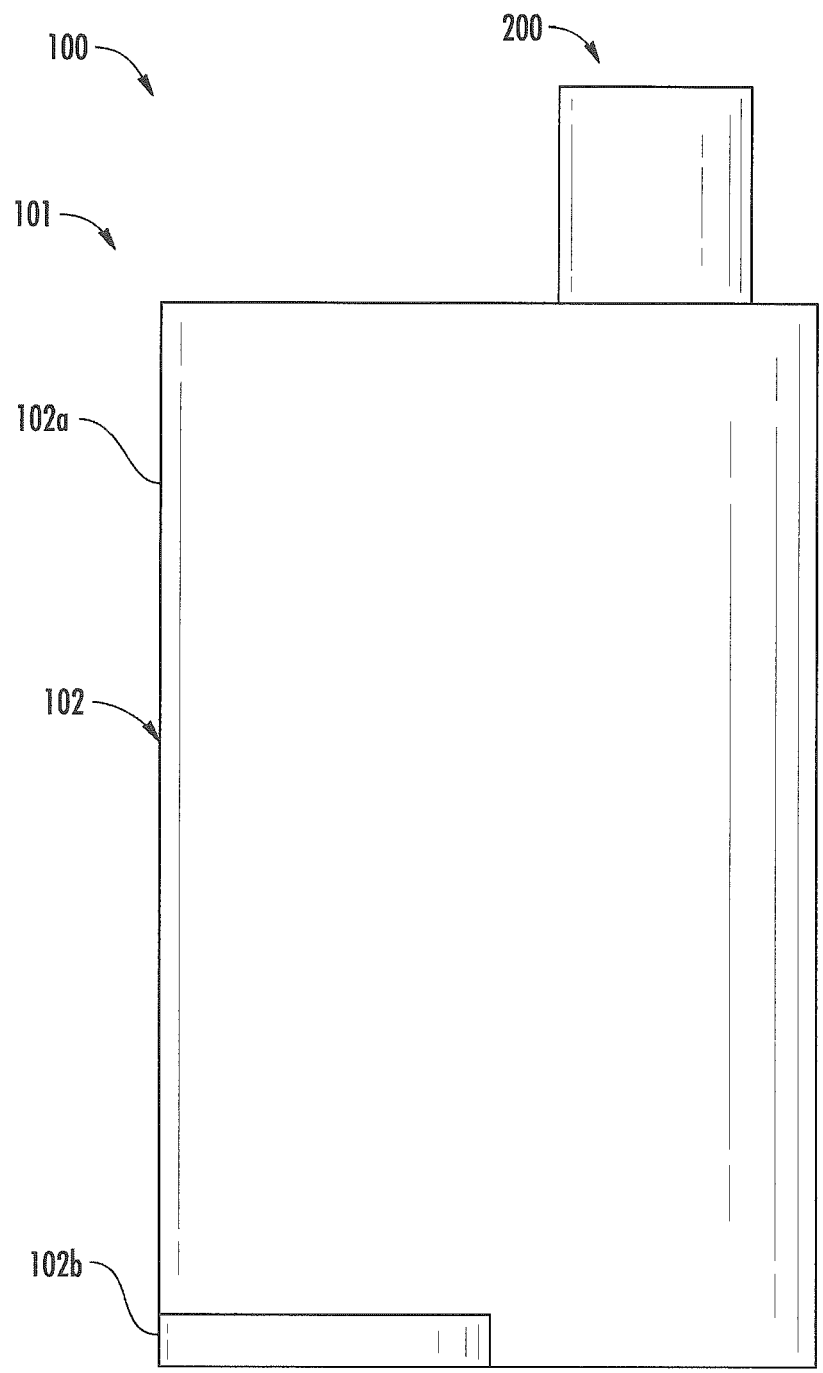
Figure 2:
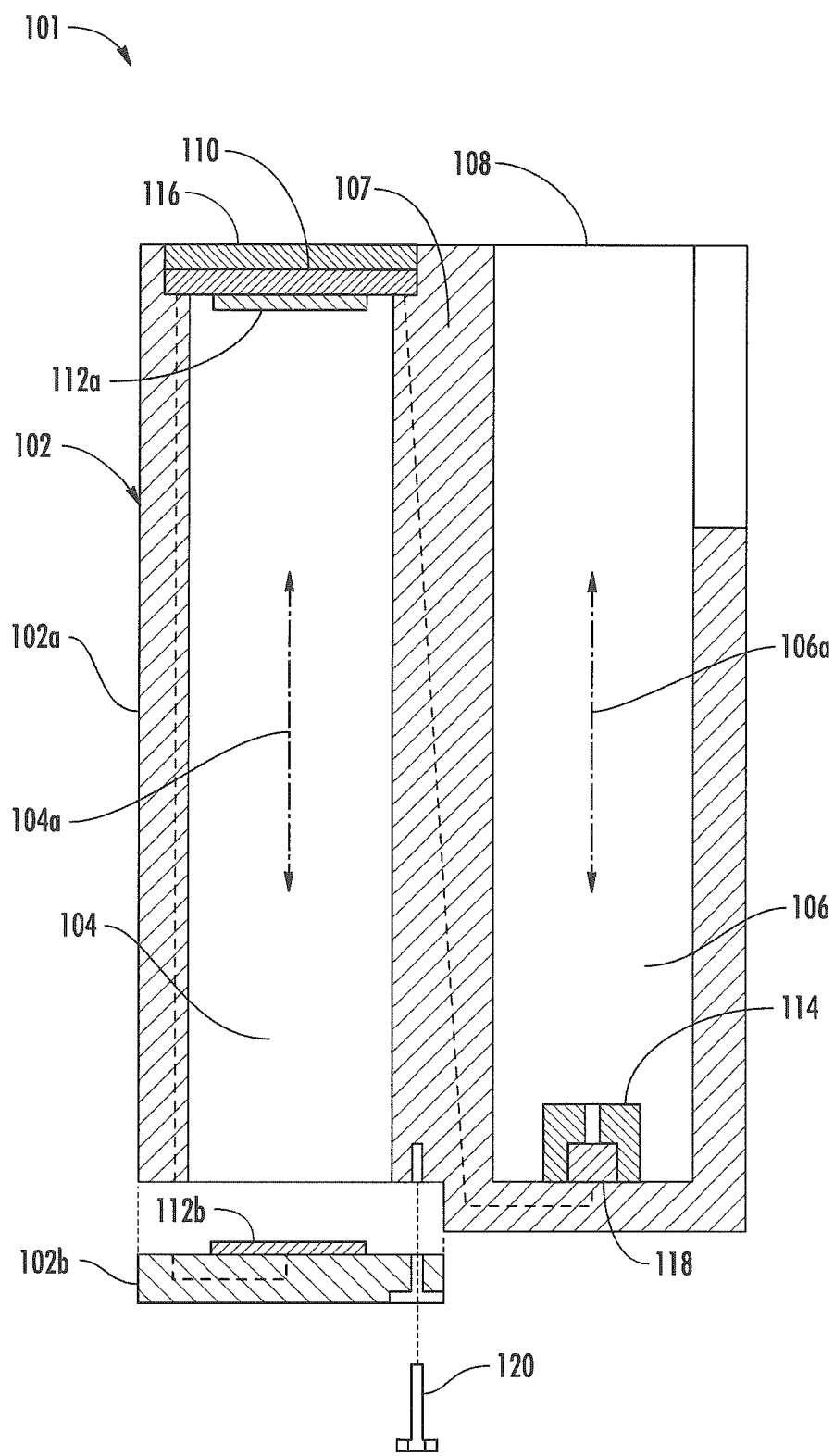
Figure 3:
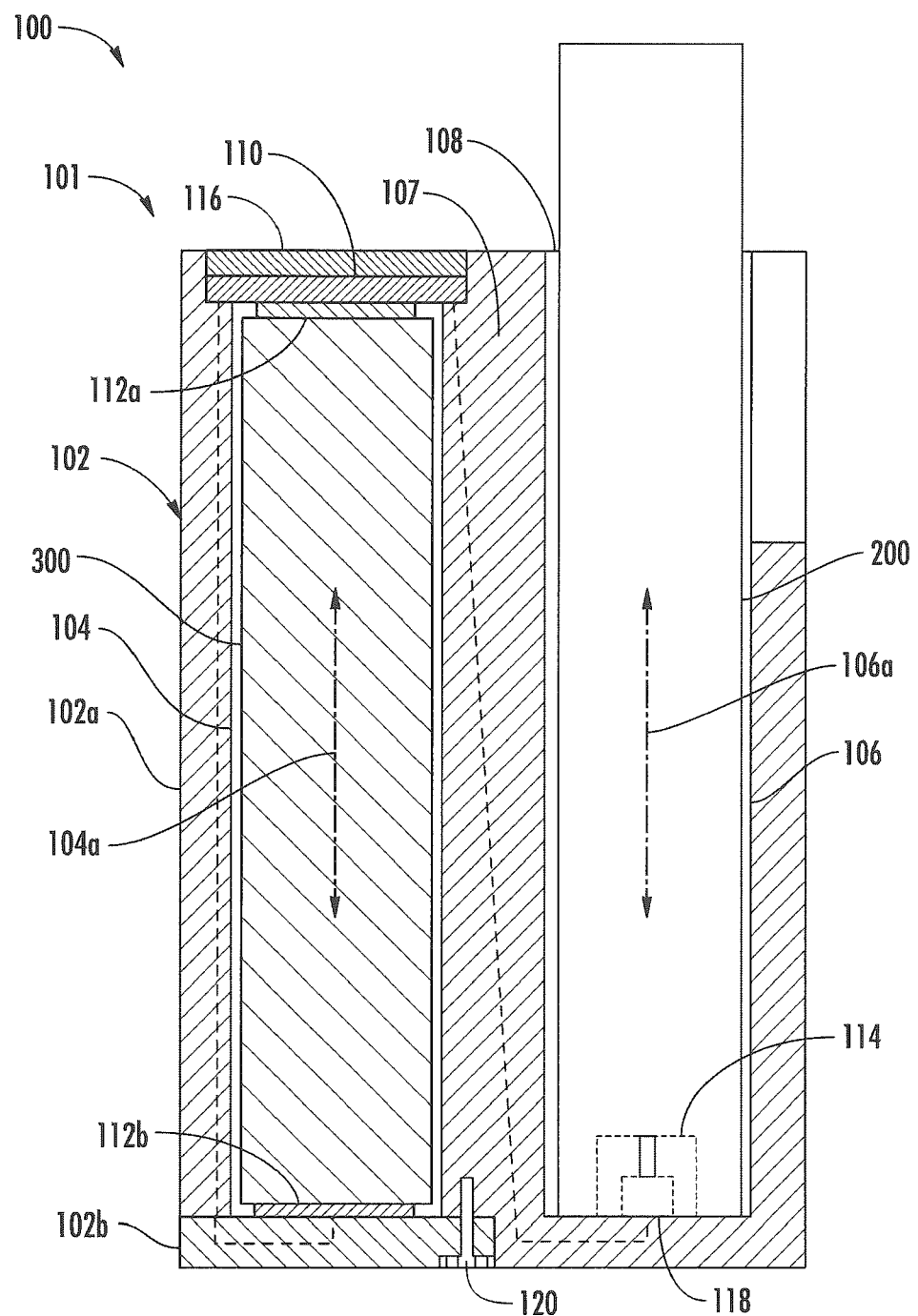
Figure 4:
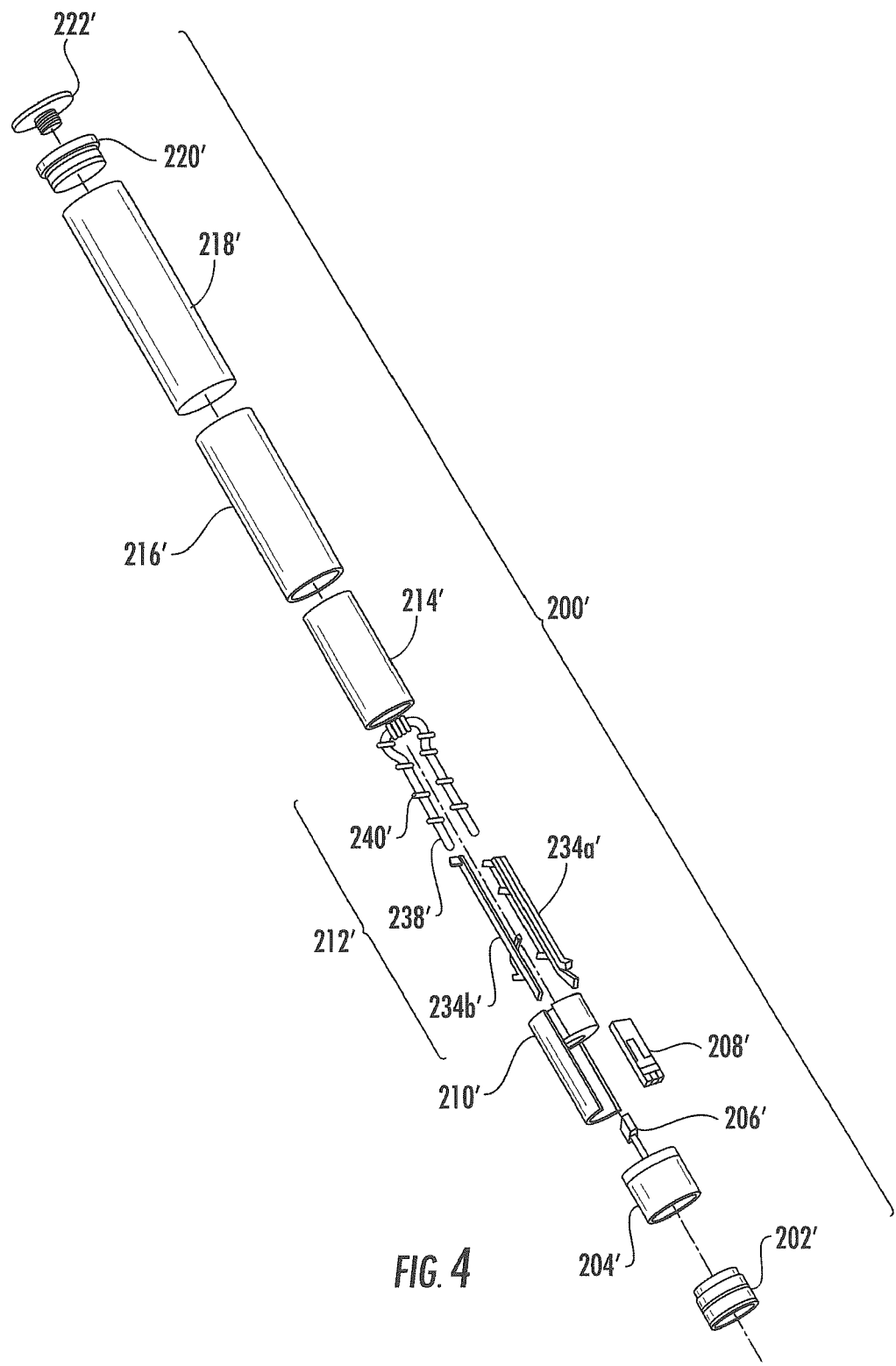
Figure 5:
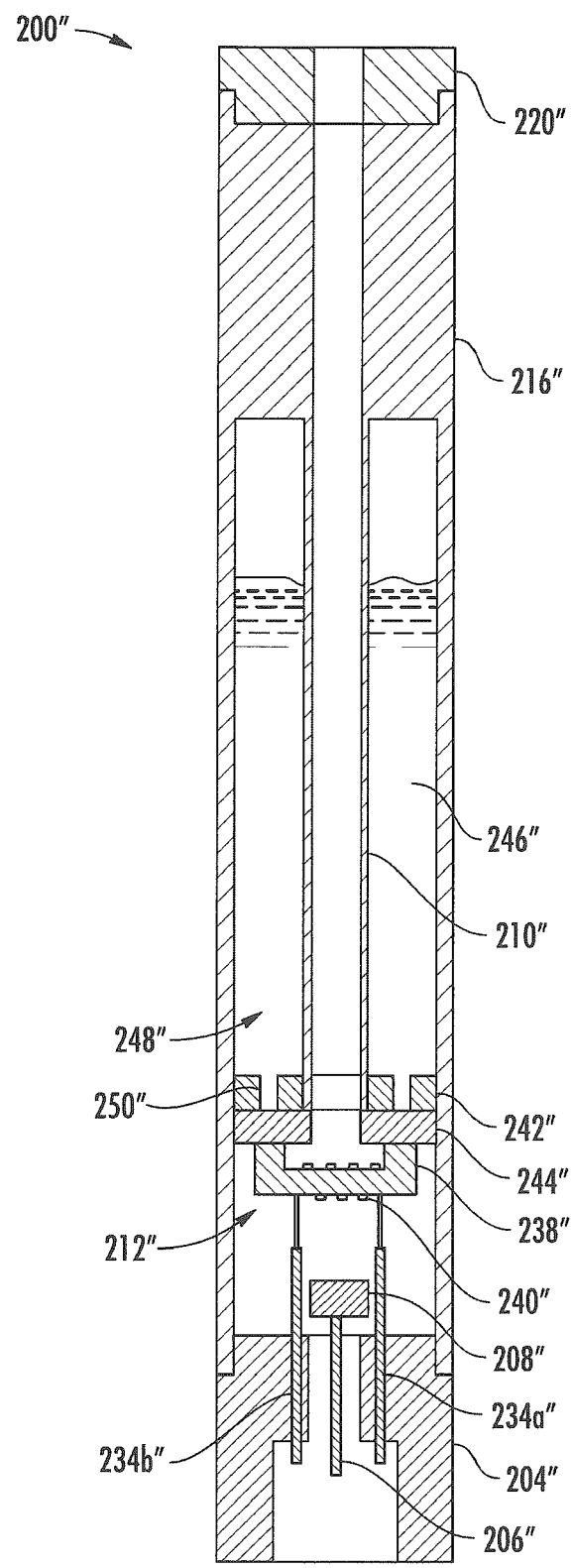
Figure 6:
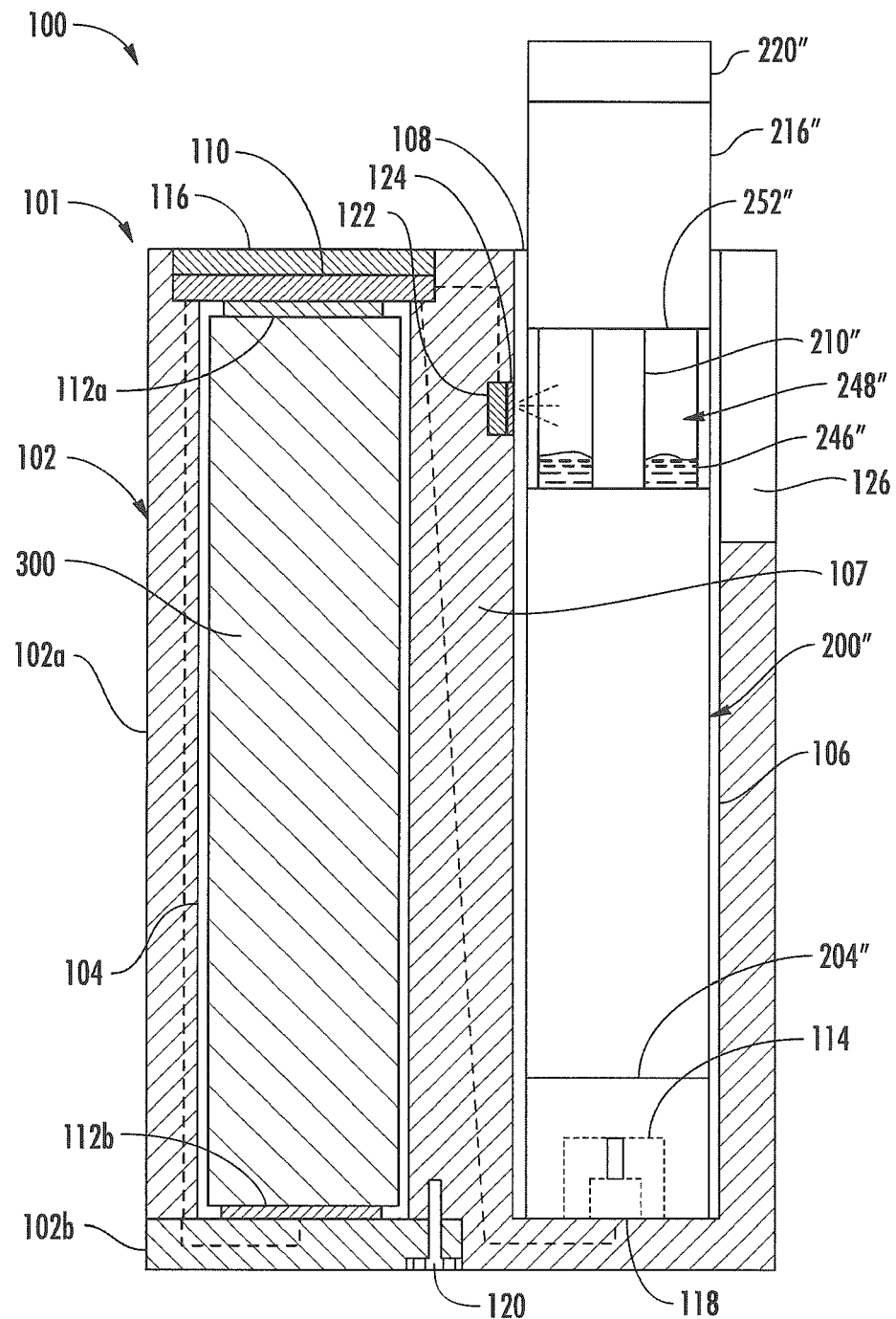
Figure 7:
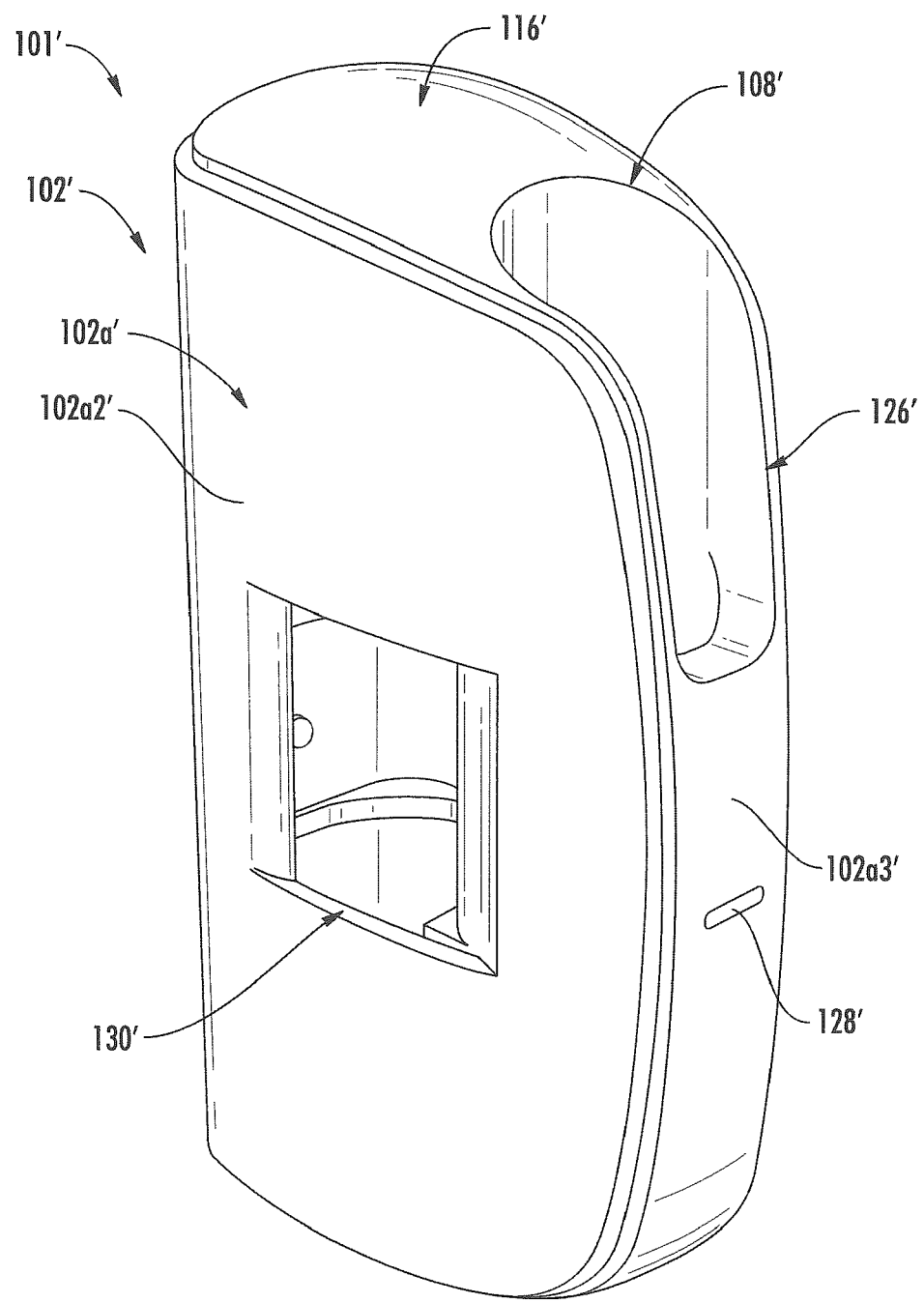
Figure 8:
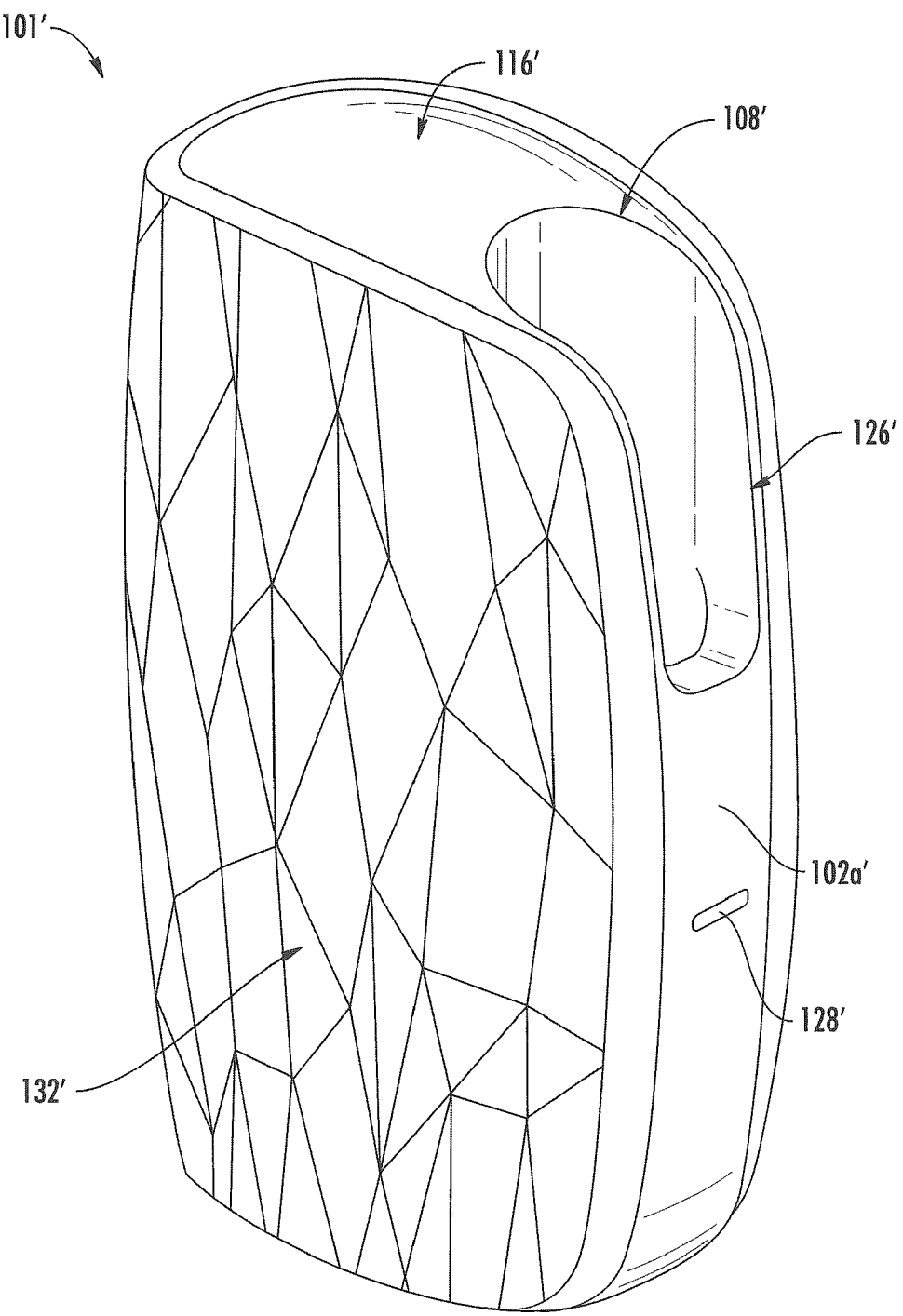
Figure 9:
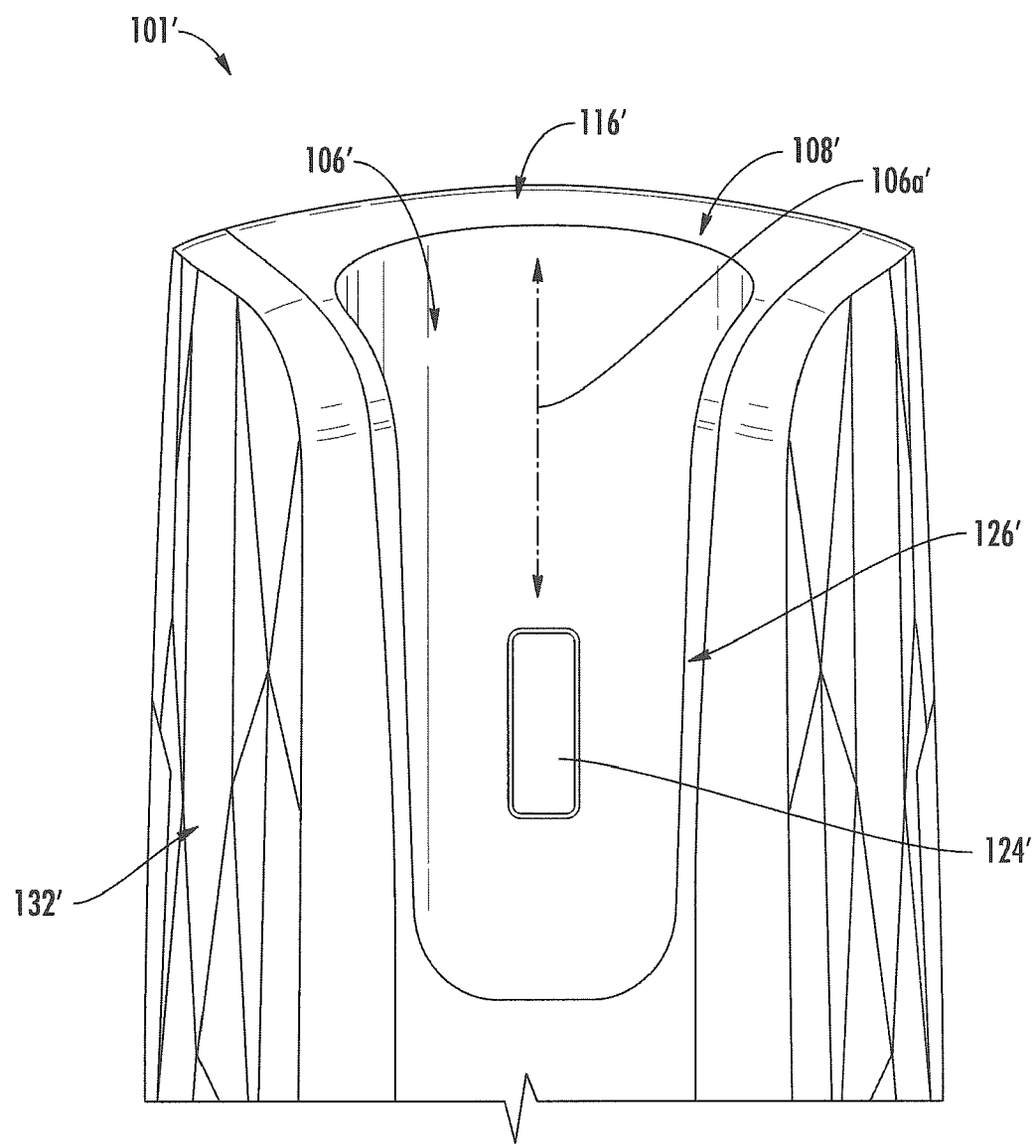
Figure 10:
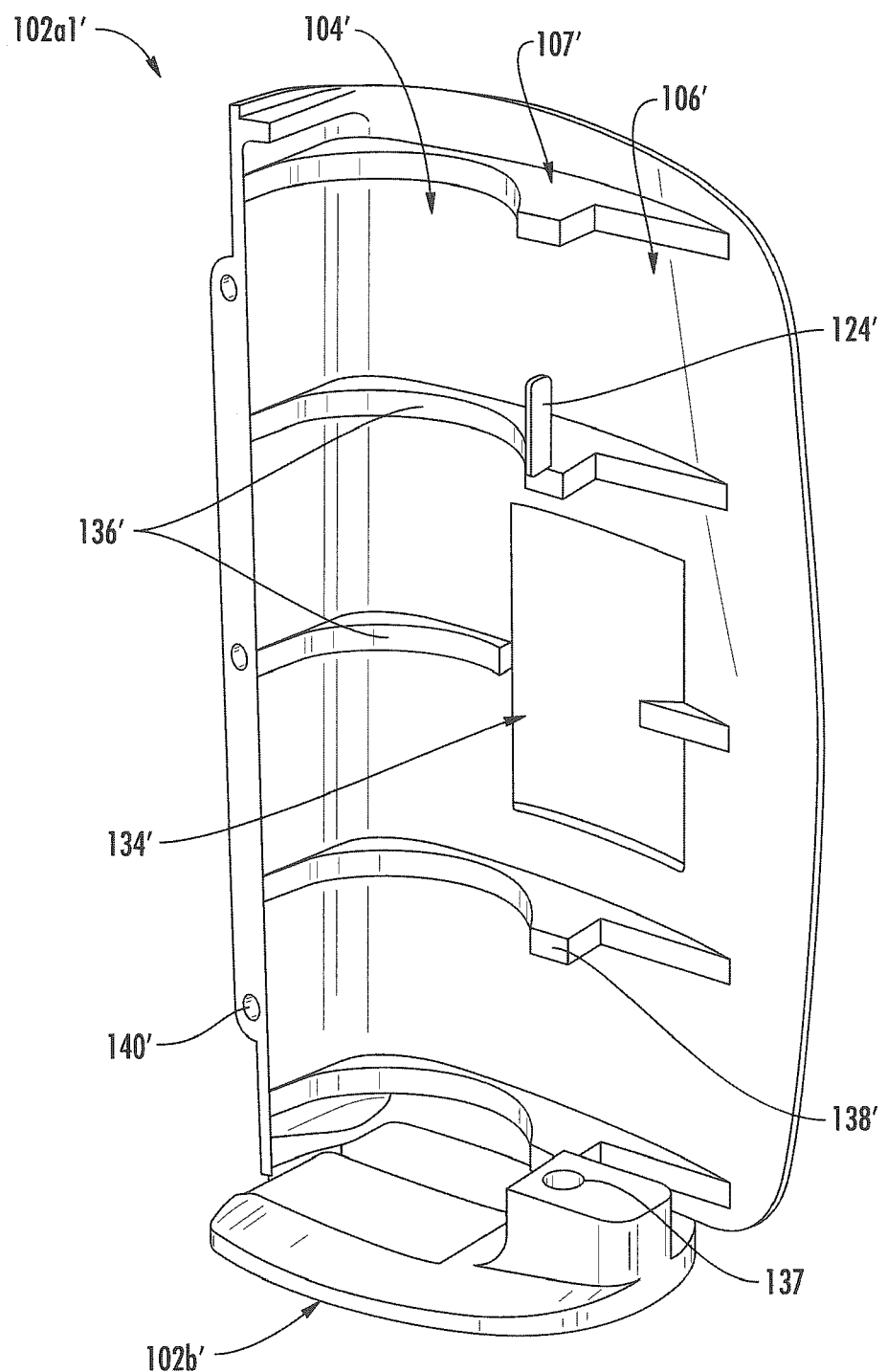
Figure 11:
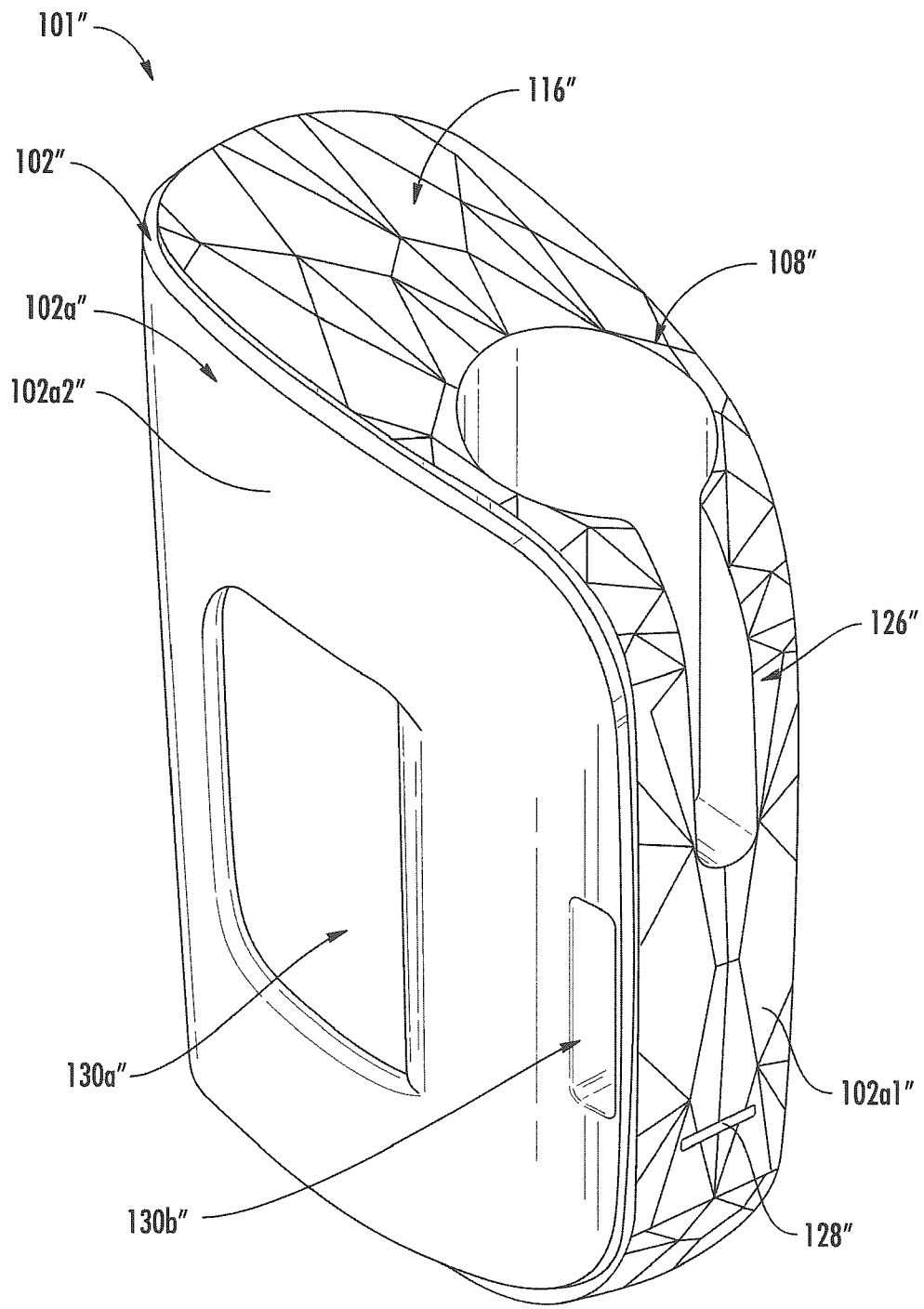
Figure 12:
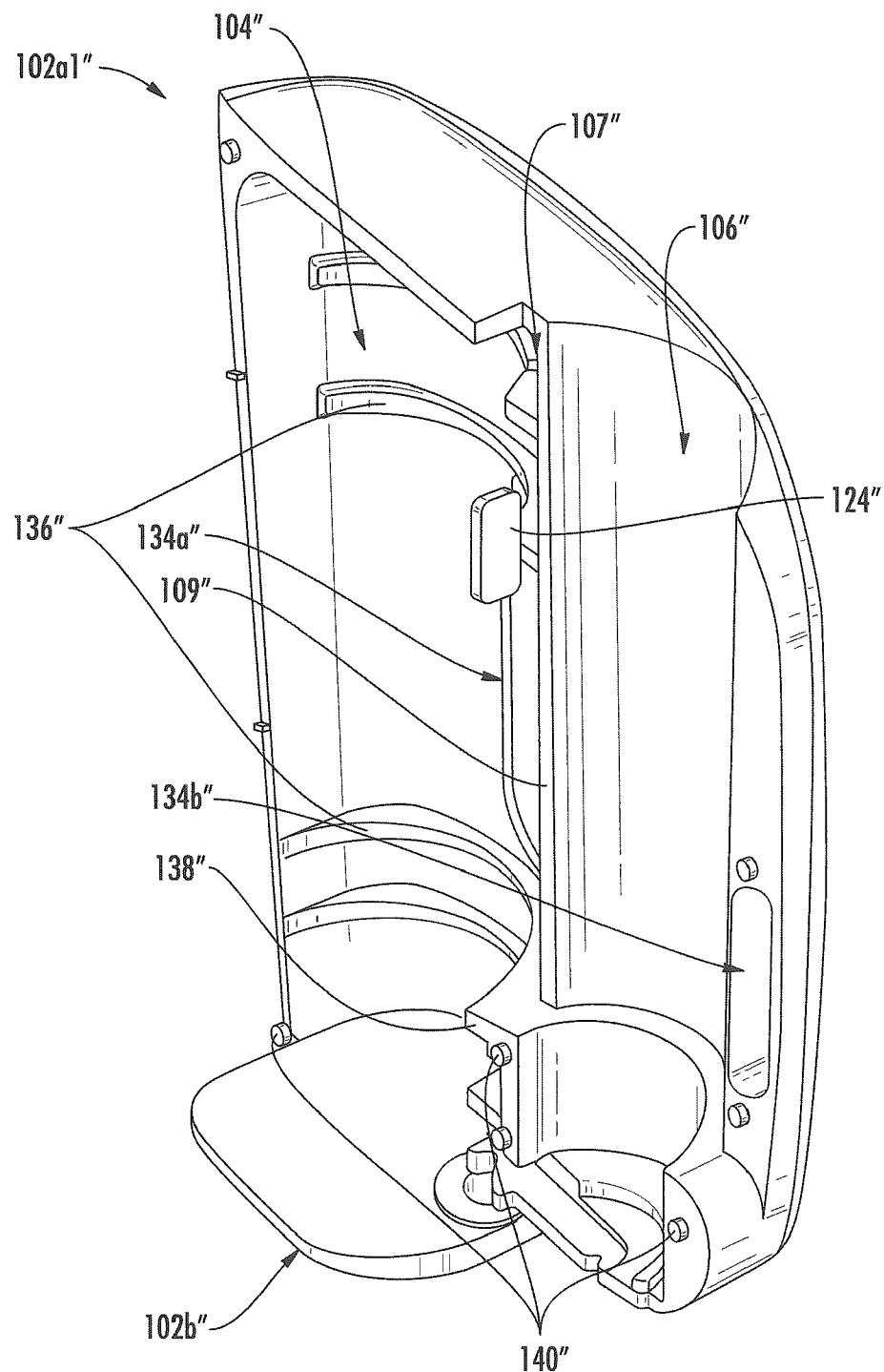
Figure 13:
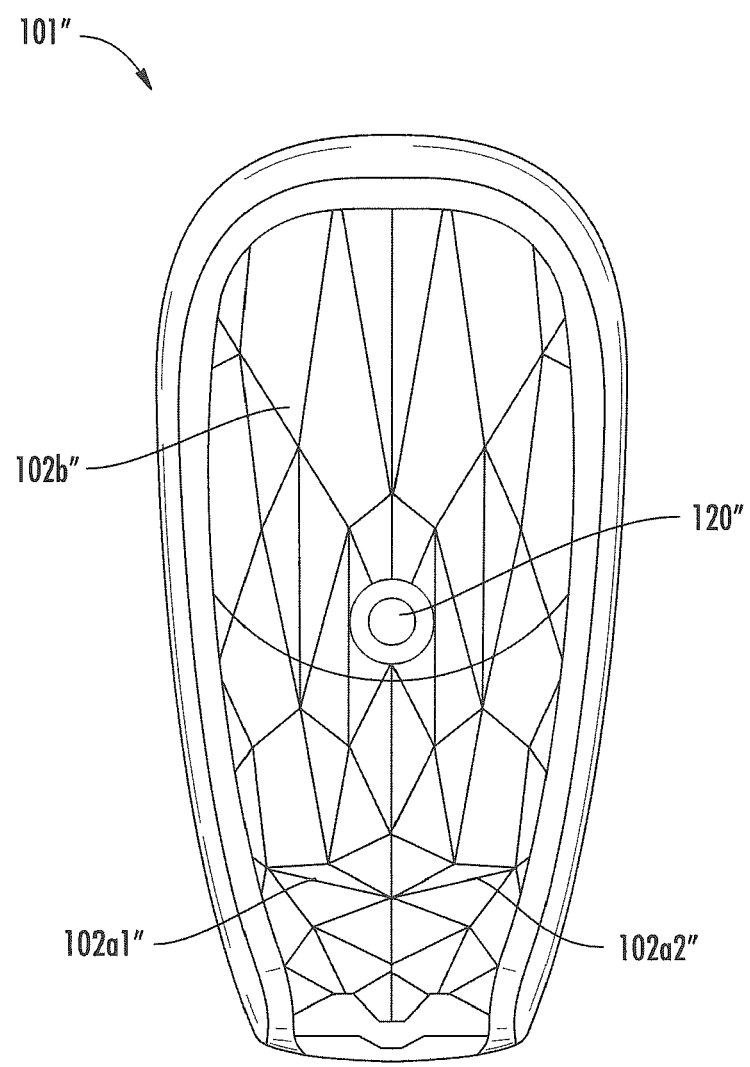
Figure 14:
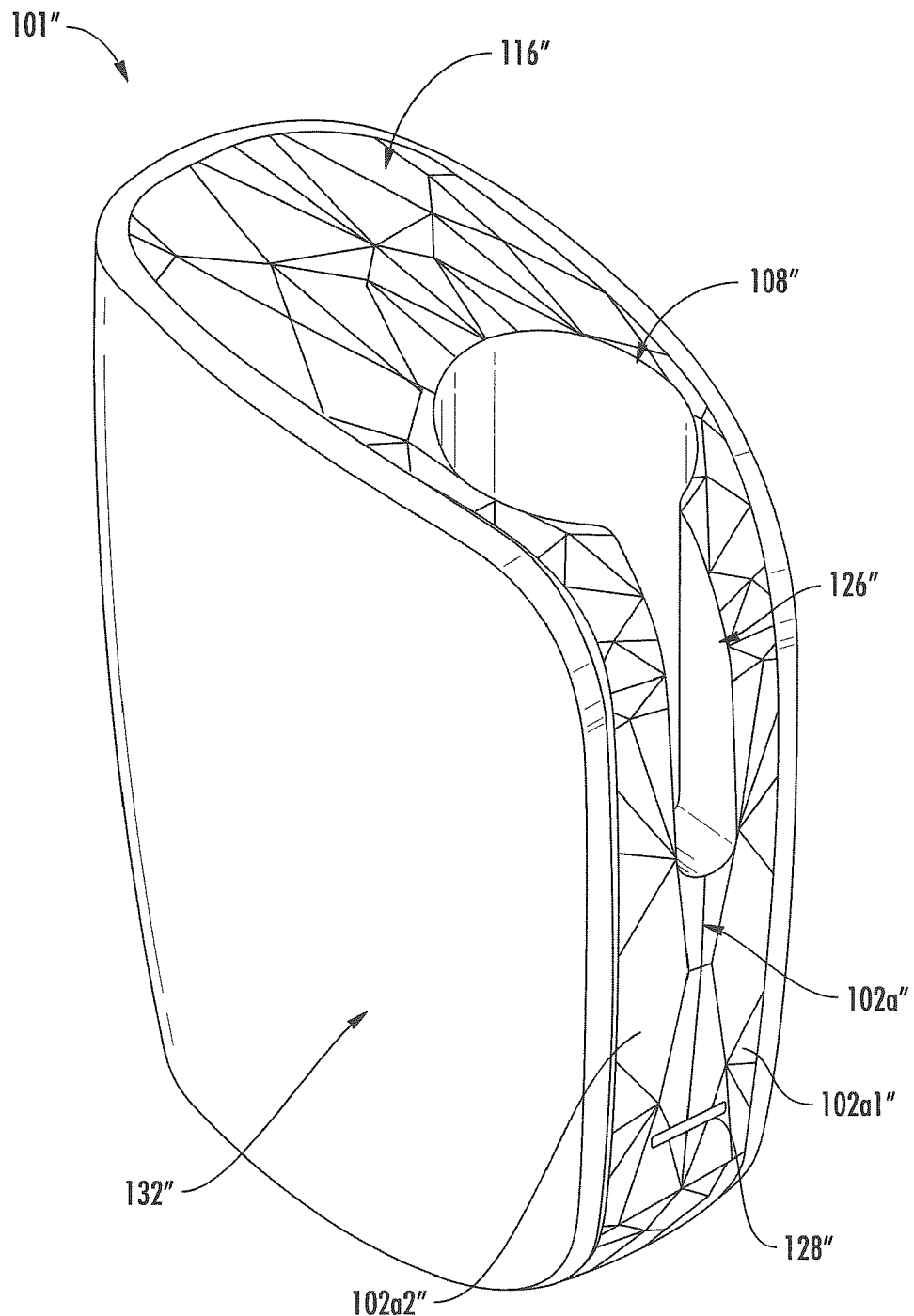
Figure 15:
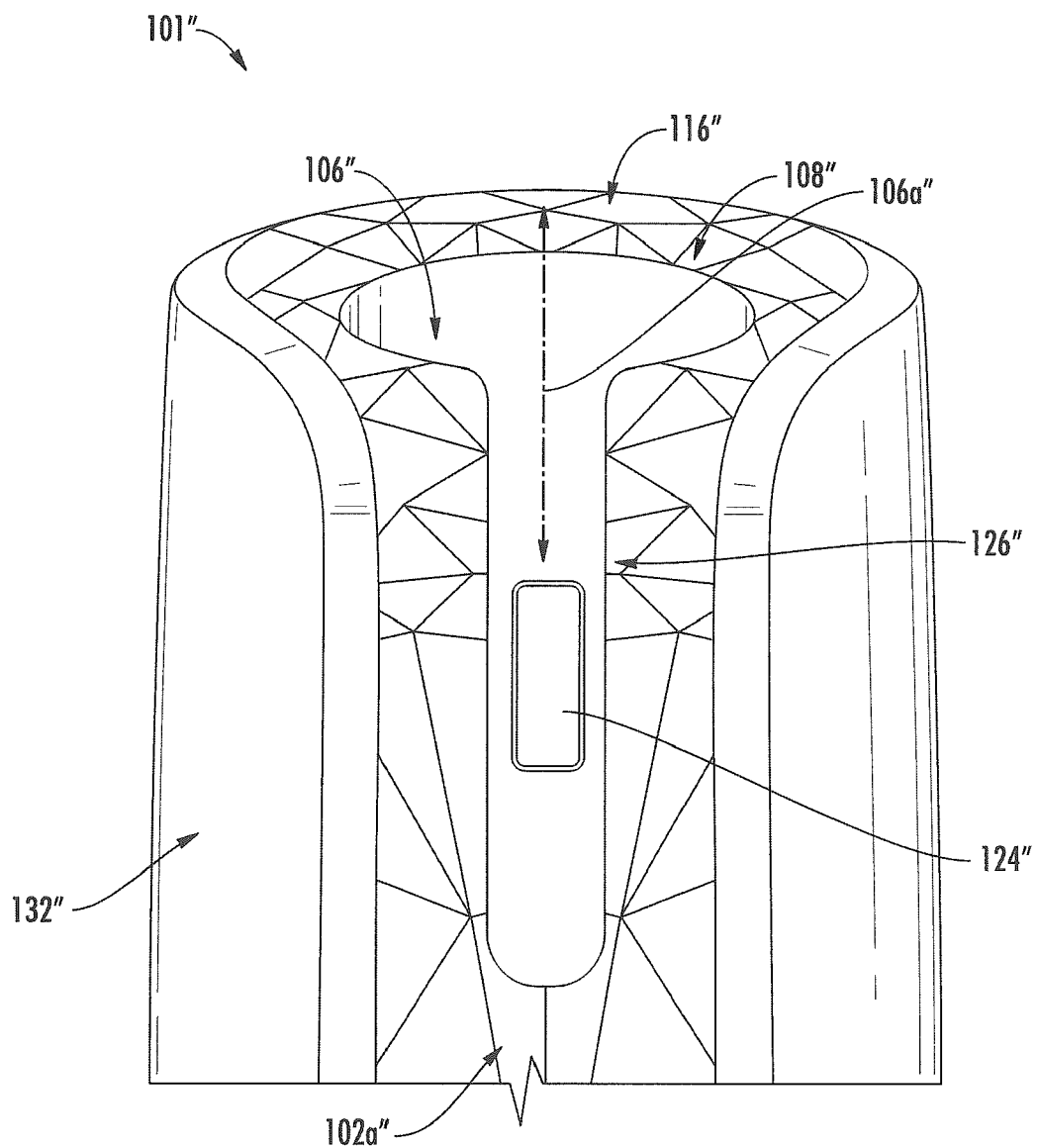
Figure 17:
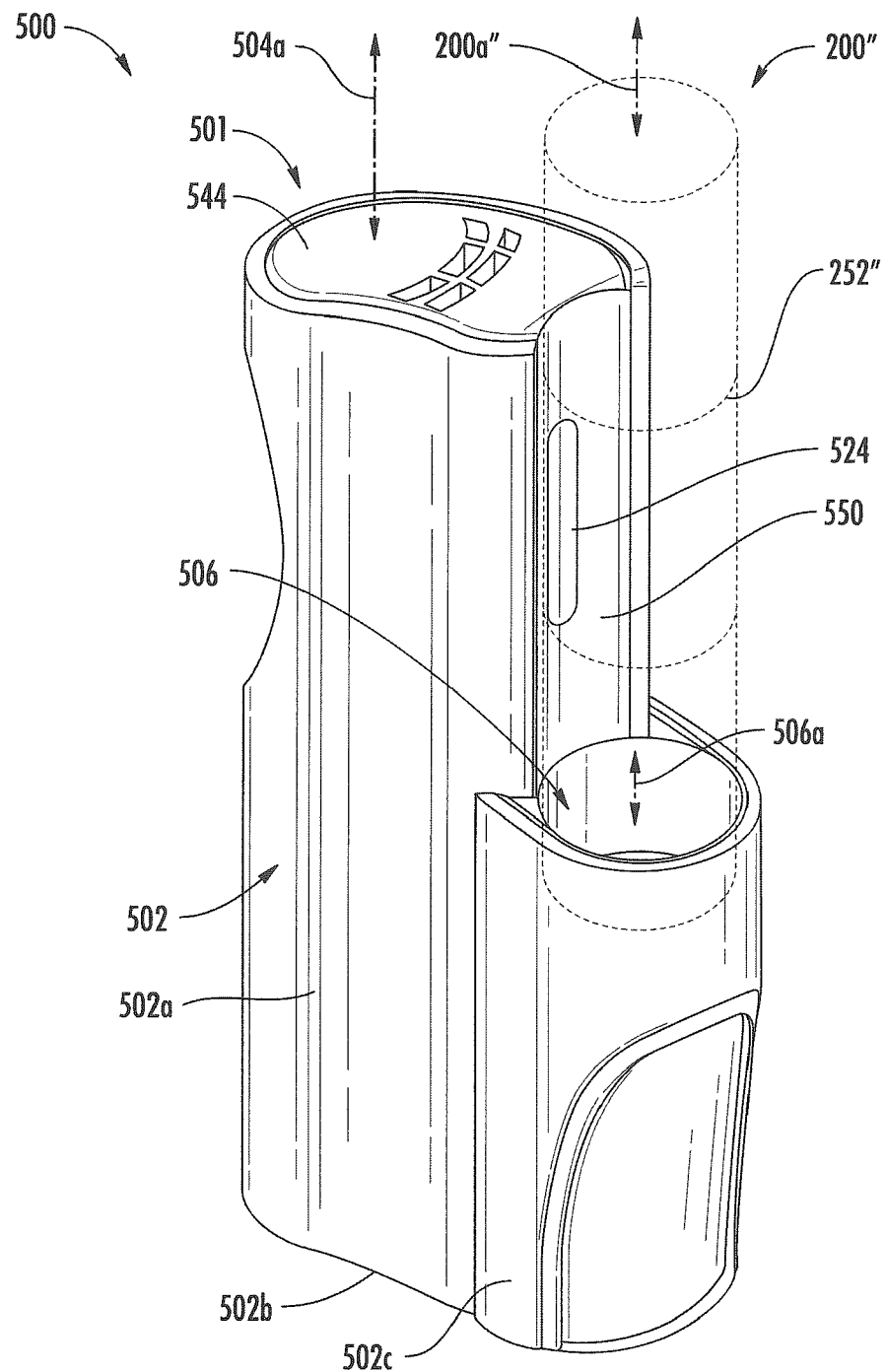
Figure 18:
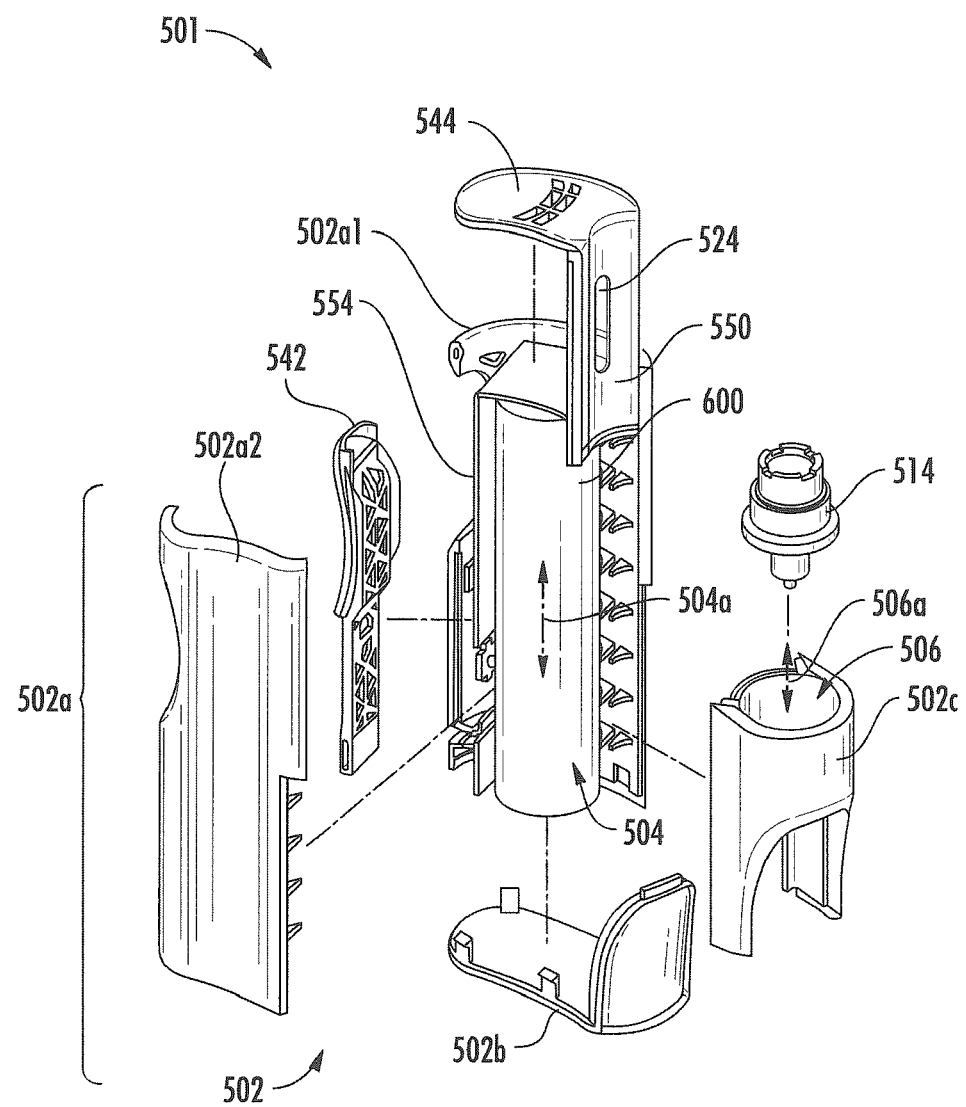
Figure 19:
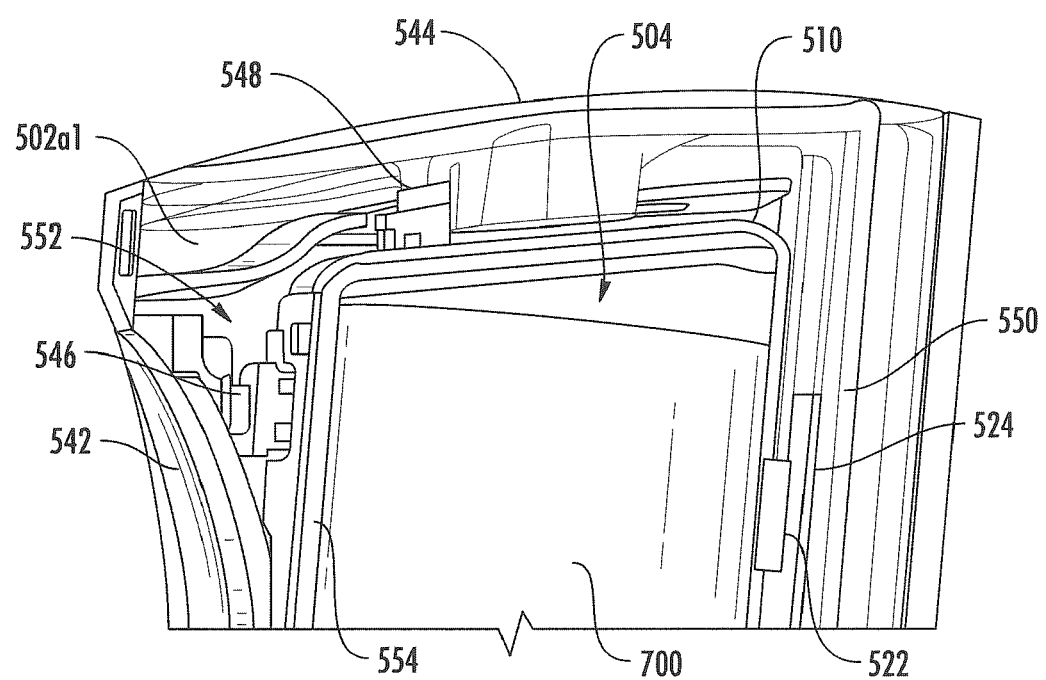
Figure 20:
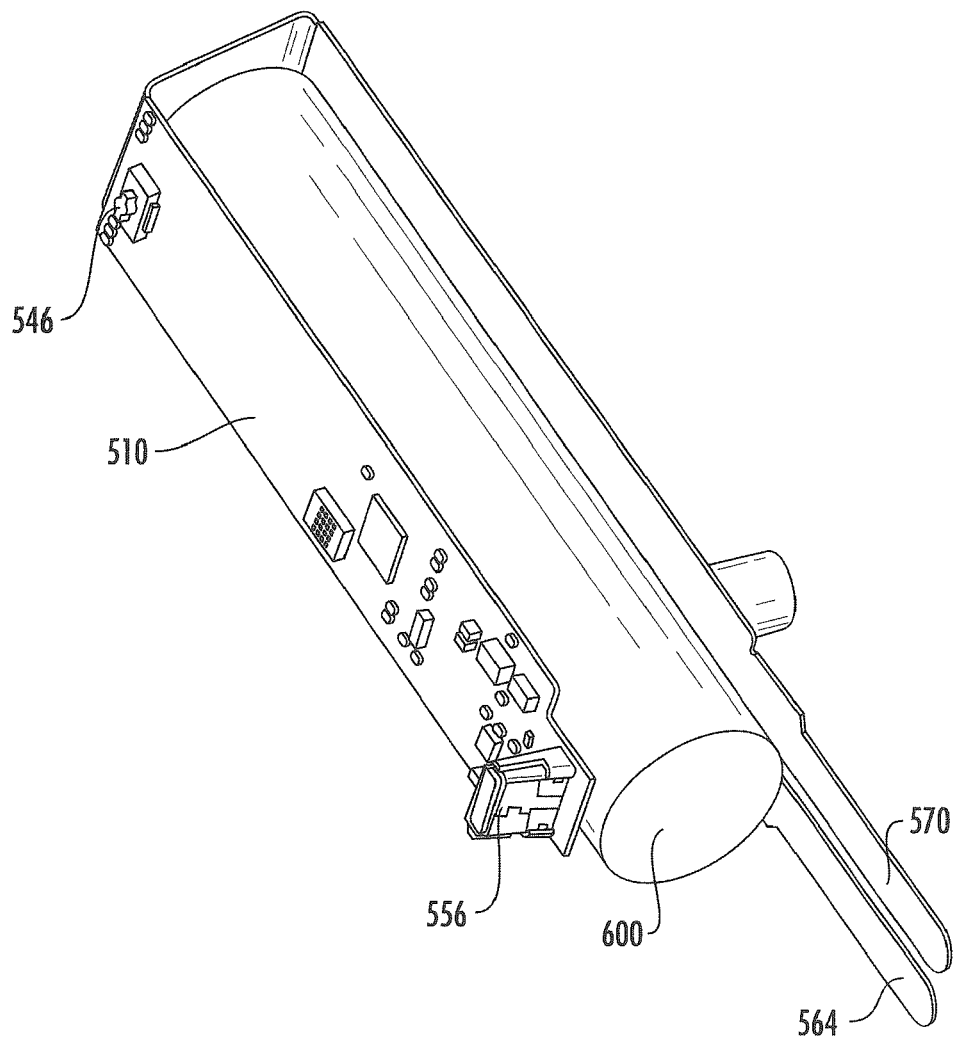
Figure 21:
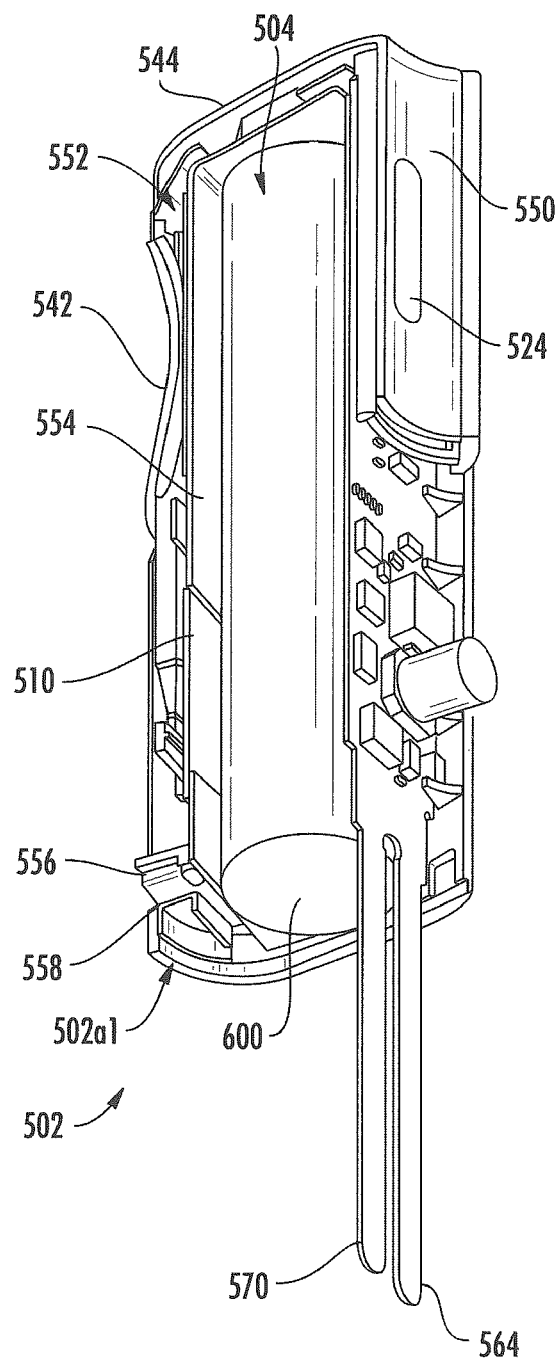
Figure 22:
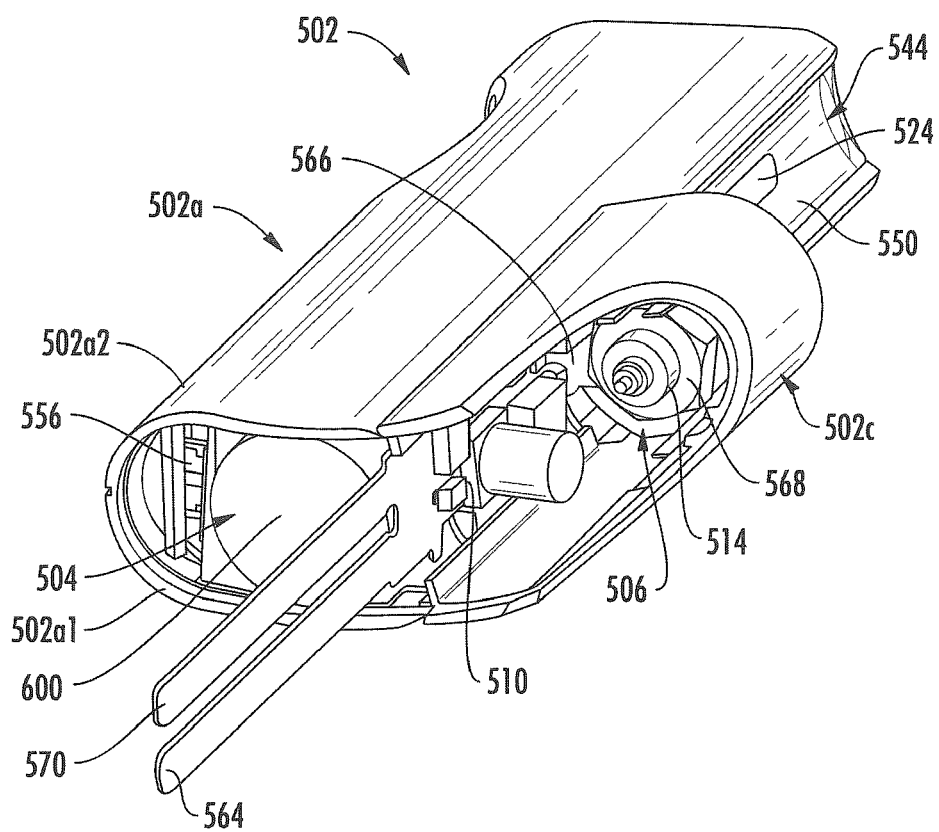
Figure 23:
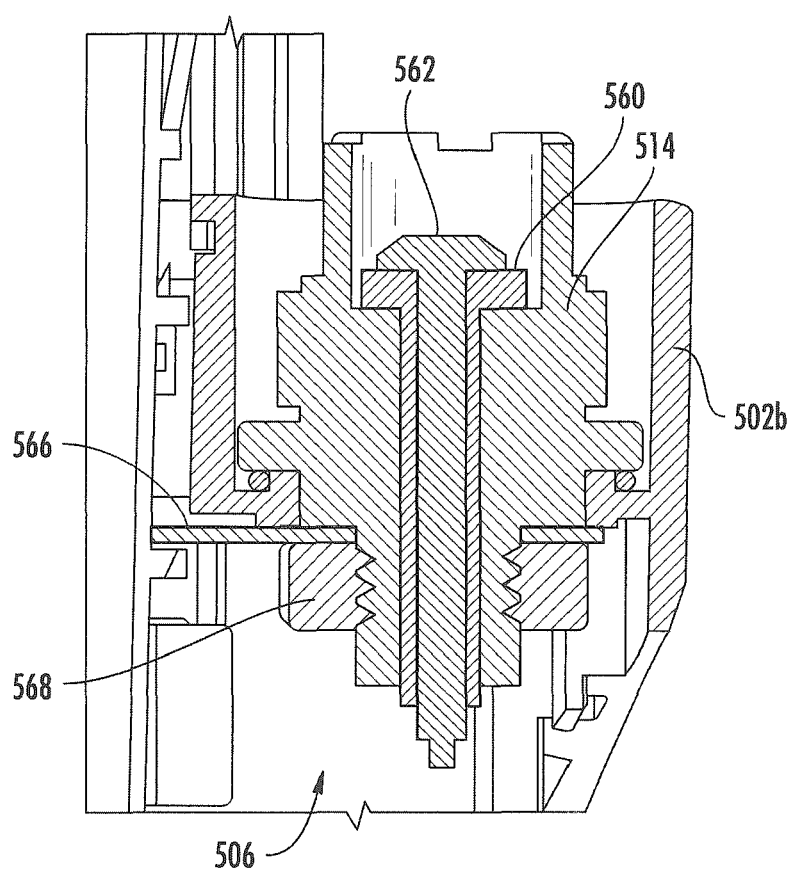
Figure 24:
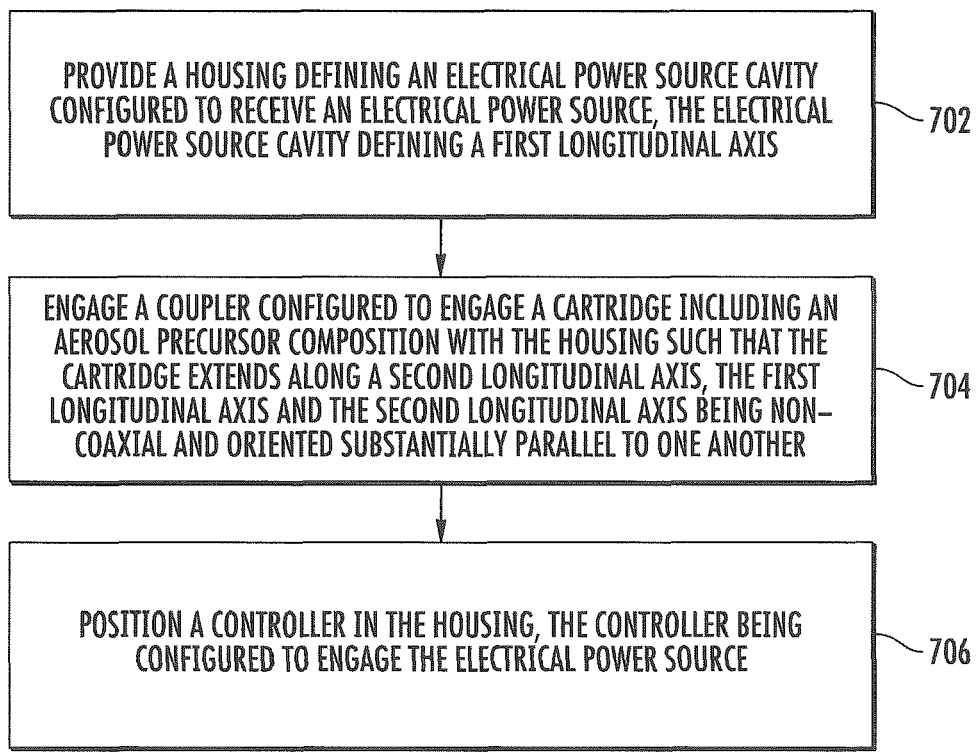

Having thus described the disclosure in the foregoing general terms, reference will now be made to the accompanying drawings, which are not necessarily drawn to scale, and wherein:

FIG. 1 illustrates a side view of an aerosol delivery device including a control body and a cartridge according to an example embodiment of the present disclosure;

FIG. 2 illustrates a sectional, partially-exploded view through the control body of the aerosol delivery device of FIG. 1 according to an example embodiment of the present disclosure;

FIG. 3 illustrates a modified sectional view through the aerosol delivery device of FIG. 1 according to an example embodiment of the present disclosure;

FIG. 4 illustrates an exploded view of an example embodiment of the cartridge of FIG. 1 including a reservoir substrate;

FIG. 5 illustrates a sectional view through an alternative example embodiment of the cartridge of FIG. 1 including a reservoir according to an example embodiment of the present disclosure;

FIG. 6 illustrates a modified sectional view through the aerosol delivery device of FIG. 1 including the cartridge of FIG. 5 according to an example embodiment of the present disclosure;

FIG. 7 illustrates a perspective view of a control body including a side opening configured to engage an outer cover and a relatively wide viewing opening according to an additional example embodiment of the present disclosure;

FIG. 8 illustrates a perspective view of the control body of FIG. 7 with the outer cover according to an example embodiment of the present disclosure;

FIG. 9 illustrates an enlarged side view of the control body of FIG. 8 at the viewing opening according to an example embodiment of the present disclosure;

FIG. 10 illustrates a section of a body portion of a housing of the control body of FIG. 7 according to an example embodiment of the present disclosure;

FIG. 11 illustrates a perspective view of a control body including side openings configured to engage an outer cover and a relatively narrow viewing opening according to an additional example embodiment of the present disclosure;

FIG. 12 illustrates a section of a body portion of a housing of the control body of FIG. 11 according to an example embodiment of the present disclosure;

FIG. 13 illustrates a bottom view of the control body of FIG. 11 according to an example embodiment of the present disclosure;

FIG. 14 illustrates the control body of FIG. 11 with the outer cover according to an example embodiment of the present disclosure;

FIG. 15 illustrates an enlarged side view of the control body of FIG. 14 at the viewing opening according to an example embodiment of the present disclosure;

FIG. 16 illustrates a method for assembling an aerosol delivery device according to an example embodiment of the present disclosure;

FIG. 17 illustrates a perspective view of an aerosol delivery device including a control body and a cartridge according to an example embodiment of the present disclosure;

FIG. 18 illustrates a partial exploded view of the control body of FIG. 17 according to an example embodiment of the present disclosure;

FIG. 19 illustrates a partial side view of the control body of FIG. 17 in a partially-assembled configuration including a first body portion of a housing thereof according to an example embodiment of the present disclosure;

FIG. 20 illustrates a perspective view of a controller and an electrical power source of the control body of FIG. 17 according to an example embodiment of the present disclosure;

FIG. 21 illustrates a perspective view of the control body of FIG. 17 in a partially-assembled configuration including a first body portion of a housing thereof according to an example embodiment of the present disclosure;

FIG. 22 illustrates a perspective view of the control body of FIG. 17 in a partially-assembled configuration including an electrical power source housing portion and a coupler portion of a housing thereof according to an example embodiment of the present disclosure;

FIG. 23 illustrates a sectional view through a coupler of the control body of FIG. 17 according to an example embodiment of the present disclosure; and FIG. 24 illustrates a method for assembling an aerosol delivery device according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

Aerosol delivery devices according to the present disclosure may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the foul' of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, an aerosol delivery device of the present disclosure can be hand-held by a user, a user can draw on a portion of the article for inhalation of aerosol produced by that article, a user can take puffs at selected intervals of time, and the like.

Aerosol delivery devices of the present disclosure generally include a housing and a number of additional components coupled thereto and/or positioned within the housing, and some of the components may be removable or replaceable. The overall design of the housing can vary, and the overall size and shape of the housing can vary. The smoking articles can include a cartridge, which can be defined by an outer body or cover—e.g., an elongated body resembling the shape of a portion of a cigarette or cigar. For example, an outer cover or body of the cartridge can be substantially tubular in shape and, as such, resemble the shape of a conventional cigarette or cigar. In some embodiments, the housing may contain one or more reusable components (e.g., a rechargeable battery and various electronics for controlling the operation of that article), and the cartridge can be removable, refillable, and/or disposable.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience. A battery for use in the present devices may be replaceable, removable, and/or rechargeable and thus may be combined with any type of recharging technology, including connection to a typical alternating current electrical outlet, connection to a car charger (i.e., a cigarette lighter receptacle), and connection to a computer, such as through a universal serial bus (USB) cable or connector. In one preferred embodiment the electrical power source comprises a lithium-ion battery, which may light weight, rechargeable, and provide a large energy storage capacity. Examples of electrical power sources are described in U.S. Pat. App. Pub. No. 2010/0028766 to Peckerar et al., the disclosure of which is incorporated herein by reference in its entirety.

An aerosol delivery device according to the present disclosure preferably incorporates a sensor or detector for control of supply of electric power to a heat generation element when aerosol generation is desired (e.g., upon draw during use). As such, for example, there is provided a manner or method for turning off the power supply to the heat generation element when the aerosol generating piece is not be drawn upon during use, and for turning on the power supply to actuate or trigger the generation of heat by the heat generation element during draw. For example, with respect to a flow sensor, representative current regulating components and other current controlling components including various microcontrollers, sensors, and switches for aerosol delivery devices are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al.; U.S. Pat. No. 8,205,622 to Pan; and U.S. Pat. No. 8,881,737 to Collet et al.; U.S. Pat. Pub. Nos. 2009/0230117 to Fernando et al.; and 2014/0270727 to Ampolini et al.; and 2015/0257445 to Henry et al.; which are incorporated herein by reference in their entireties. Additional representative types of sensing or detection mechanisms, structures, components, configurations, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some embodiments, the aerosol delivery device can include an indicator, which may comprise one or more light emitting diodes. The indicator can be in communication with the control component through a connector circuit and illuminate, for example, during a user draw on the mouthend as detected by the flow sensor.

Various elements that may be included in the housing are described in U.S. App. Pub. No. 2015/0245658 to Worm et al., which is incorporated herein by reference in its entirety. Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to a pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 to Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; WO 2013/089551 to Foo; and U.S. Pat. App. Pub. No. 2014/0261408 to DePiano et al., each of which is incorporated herein by reference in its entirety.

The aerosol precursor composition, also referred to as a vapor precursor composition, may comprise a variety of components including, by way of example, any of a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.;

and Chemical and Biological Studies on New Cigarette Prototypes that Heat Instead of Burn Tobacco, R. J. Reynolds Tobacco Company Monograph (1988); the disclosures of which are incorporated herein by reference in their entireties. Other aerosol precursors which may be employed in the aerosol delivery device of the present disclosure include the aerosol precursors included in the VUSE® product by R. J. Reynolds Vapor Company, the BLU™ product by Lorillard Technologies, the Mistic Menthol product by Mistic Ecigs, and the Vype product by CN Creative Ltd. Also desirable are the so-called "Smoke Juices" for electronic cigarettes that have been available from Johnson Creek Enterprises LLC. Additional exemplary formulations for aerosol precursor materials that may be used according to the present disclosure are described in U.S. Pat. Pub. No. 2013/0008457 to Zheng et al., and U.S. Pat. Pub. No. 2013/0213417 to Chong et al., the disclosures of which are incorporated herein by reference in their entireties.

The aerosol delivery device preferably includes a reservoir. In some embodiments, a reservoir may comprise a container for storing a liquid aerosol precursor, a fibrous substrate, or a combination of a fibrous substrate and a container. A fibrous substrate suitable for use as a reservoir may comprise a plurality of layers of nonwoven fibers and may be formed substantially into the shape of a tube. For example, the formed tube may be shaped and sized for placement within the outer body or cover of a cartridge for use in the aerosol delivery device. Liquid components, for example, can be sorptively retained by the fibrous substrate and/or be retained within a reservoir container. The reservoir preferably is in fluid connection with a liquid transport element. Thus, the liquid transport element may be configured to transport liquid from the reservoir to a heating element, such as via capillary action and/or via active transport—e.g., pumping or controlled movement with a valve. Representative types of substrates, reservoirs, or other components for supporting the aerosol precursor are described in U.S. Pat. No. 8,528,569 to Newton; and U.S. Pat. App. Pub. Nos. 2014/0261487 to Chapman et al.; 2014/0004930 to Davis et al.; and 2015/0216232 to Bless et al.; which are incorporated herein by reference in their entireties.

The liquid transport element may be in direct contact with the heating element. Various wicking materials, and the configuration and operation of those wicking materials within certain types of aerosol delivery devices, are set forth in U.S. Pat. No. 8,910,640 to Sears et al., which is incorporated herein by reference in its entirety. A variety of the materials disclosed by the foregoing documents may be incorporated into the present devices in various embodiments, and all of the foregoing disclosures are incorporated herein by reference in their entireties.

The heating element may comprise a wire defining a plurality of coils wound about the liquid transport element. In some embodiments the heating element may be formed by winding the wire about the liquid transport element as described in U.S. Pat. App. Pub. No. 2014/0157583 to Ward et al, which is incorporated herein by reference in its entirety. Further, in some embodiments the wire may define a variable coil spacing, as described in U.S. Pat. App. Pub. No. 2014/0270730 to DePiano et al., which is incorporated herein by reference in its entirety. Various embodiments of materials configured to produce heat when electrical current is applied therethrough may be employed to form the heating element. Example materials from which the wire coil may be formed include titanium, platinum, silver, palladium, Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). The heating element may comprise a wire defining a mesh, screen or lattice structure positioned about the liquid transport element. Example materials from which the wire mesh, screen, or lattice may be formed include titanium, platinum, silver, palladium, Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). An example embodiment of a mesh heating element is disclosed in U.S. Pat. Appl. Pub. No. 2015/0034103 to Hon. In some embodiments, a stamped heating element may be employed in the atomizer, as described in U.S. Pat. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Embodiments of microheaters and atomizers incorporating microheaters suitable for use in the presently disclosed devices are described in U.S. Pat. No. 8,881,737 to Collett et al., which is incorporated herein by reference in its entirety.

One or more heating terminals (e.g., positive and negative terminals) may connect to the heating element so as to form an electrical connection with the power source and/or a terminal may connect to one or more control elements of the aerosol delivery device. Further, various examples of electronic control components and functions performed thereby are described in U.S. Pat. App. Pub. No. 2014/0096781 to Sears et al., which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In further embodiments, one or more components of the aerosol delivery device may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the battery and controller. An example embodiment of a carbon-based cartridge is provided in U.S. Pat. App. Pub. No. 2013/0255702 to Griffith et al., which is incorporated herein by reference in its entirety.

Aerosol delivery devices are often configured in a manner that mimics aspects of certain traditional smoking devices such as cigarettes or cigars. In this regard, aerosol delivery devices typically define a substantially cylindrical configuration. For example, aerosol delivery devices often include a control body and a cartridge which attach in an end-to-end relationship to define the substantially cylindrical configuration. While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, such configurations may result in a relatively large device when employed with reservoirs having relatively large capacity, resembling the size and shape of a cigar, which may not be suitable for temporary storage or transport in a user's pocket.

So-called "mod" devices may include configurations other than parallel, coaxial alignment of a control body and a cartridge. However, such devices may include exposed and/or poorly-supported electrical connectors that connect the control body and cartridge, which may be strained during use or storage, thereby potentially affecting the usability thereof. Accordingly, it may be desirable to provide aerosol delivery devices in configurations and shapes that differ from configurations and shapes associated with traditional smoking articles and traditional aerosol delivery devices.

As such, embodiments of the present disclosure provide alternative aerosol delivery devices configured to address the above-noted deficiencies of existing configurations of aerosol delivery devices and/or provide other benefits. FIG. 1 illustrates a side view of an aerosol delivery device 100 of the present disclosure. As illustrated, the aerosol delivery device 100 may include a control body 101, which may include a housing 102. In some embodiments the housing may comprise a plastic material, but various other materials, which are preferably substantially rigid, may be employed in other embodiments. The housing 102 may be unitary or comprise multiple pieces. For example, the housing 102 may include a body portion 102a, which may itself comprise one or more pieces, and an access door 102b. As further illustrated in FIG. 1, the aerosol delivery device 100 may additionally include a cartridge 200, which may be at least partially received in the control body 101.

FIG. 2 illustrates a partially-exploded sectional view through the control body 101 of the aerosol delivery device 100. As illustrated, the housing 102 may define an electrical power source cavity 104. In particular, the electrical power source cavity 104 may be defined in the body portion 102a of the housing 102. The electrical power source cavity 104 may be closed by, and accessed via, the access door 102b. As described below, the electrical power source cavity 104 may be configured to receive an electrical power source.

Further, the housing 102 may define a cartridge cavity 106. As described in detail below, the cartridge cavity 106 may be configured to receive the cartridge 200 (see, e.g., FIG. 3). In this regard, the housing 102 may define an external opening 108 at the cartridge cavity 106 configured to receive the cartridge 200 therethrough.

The housing 102 may include a divider wall 107 that separates the power source cavity 104 from the cartridge cavity 106. In some embodiments the divider wall 107 completely separates the power source cavity 104 from the cartridge cavity 106. For example, the divider wall 107 may extend across the length and thickness of the control body 101 such that the power source cavity 104 and the cartridge cavity 106 are discrete cavities. This configuration may be preferable in that it may prevent fluid communication between the power source cavity 104 and the cartridge cavity 106. Thereby, for example, in the event of a structural failure of the electrical power source, chemical intrusion into the cartridge cavity 106 may be resisted. However, as may be understood, in other embodiments the divider wall may be discontinuous in one or both of length and fitness. Such a configuration of the divider wall may still respectively retain an electrical power source in the electrical power source cavity and a cartridge in the cartridge cavity such that these components are securely retained in place.

The control body 101 may include one or more additional components. The components may be received in, or otherwise engaged with, the housing 102. For example, the components may include an electrical circuit, the operation of which is described below. The electrical circuit may include a controller 110, first and second electrical contacts 112a, 112b, and a coupler 114. In some embodiments the electrical circuit may additionally include an electronic display 116 (e.g., a liquid crystal display). Further, the electrical circuit may include a flow sensor 118, which may be positioned at, or in fluid communication with, the coupler 114. Wires or other electrical connectors may provide connections between the various components of the electrical circuit. In some embodiments the electrical circuit may further comprise a communication module. The communication module may be configured to communicate via Bluetooth or any other communication standard. Examples of communication modules and related antenna components which may be included in the aerosol delivery device 100 are described in U.S. patent application Ser. No. 14/802,789, filed Jul. 17, 2015, and Ser. No. 14/638,562, filed Mar. 4, 2015, each to Marion et al.

FIG. 3 illustrates a sectional view through the aerosol delivery device 100. As illustrated, the cartridge 200 may be at least partially received in the cartridge cavity 106 when engaged with the control body 101. In this regard, the cartridge 200 may be inserted through the external opening 108 into the cartridge cavity 106. As the cartridge 200 is inserted into the cartridge cavity 106, the cartridge 200 may engage the coupler 114. Thereby, the cartridge 200 may establish an electrical connection with the control circuit such that current may be selectively directed to the cartridge by the controller 110 to produce aerosol.

As further illustrated in FIG. 3, the aerosol delivery device 100 may additionally include an electrical power source 300. The electrical power source 300 may be received in the electrical power source cavity 104, and the access door 102b may be secured to the body portion 102a of the housing 102, such that the electrical power source 300 is retained in the electrical power source cavity 104. In this regard, the aerosol delivery device 100 may additionally include at least one fastener 120 (e.g., a screw) configured to retain the access door 102b in engagement with the body portion 102a of the housing 102.

When the electrical power source 300 is inserted into the electrical power source cavity 104, the first electrical contact 112a may engage a first end of the electrical power source, at which a first terminal of the electrical power source may be positioned. Thereafter, when the access door 102b is secured to the body portion 102, the second electrical contact 112b may engage an opposing second end of the electrical power source 300, at which a second terminal may be positioned. Thereby, power from the electrical power source 300 may be supplied to the controller 110. However, as may be understood, the electrical contacts 112a, 112b may be positioned and configured in other manners as appropriate for engagement with the terminals of the electrical power source 300, such that various embodiments of the electrical power source may be employed. For example, in another embodiment both of the electrical contacts may be positioned at and configured to engage either the top or the bottom of the electrical power source.

In some embodiments the electrical power source 300 may further comprise a protective circuit. Such a protective circuit may prevent overcharging of the electrical power source and/or regulate the release of current within acceptable limits. Further, the electrical power source may additionally include shock absorbing members (e.g., foam pads) in some embodiments, which may protect the electrical power source from damage associated with dropping the aerosol delivery device 100.

As further illustrated in FIGS. 2 and 3, in some embodiments the electrical power source cavity 104 and the cartridge cavity 106 may be elongated and respectively define a longitudinal axis 104a, 106a. The longitudinal axis 104a of the electrical power source cavity 104 and the longitudinal axis 106a of the cartridge cavity 106 may be substantially parallel to one another. Such a configuration may allow for receipt of both the cartridge 200 and the electrical power source 300 in a space efficient manner within the housing 102.

As noted herein, many existing embodiments of aerosol delivery devices define generally elongated, tubular configurations wherein the electrical power source and cartridge are positioned generally end to end to mimic the smoking articles such as cigarettes and cigars. Thereby, existing embodiments of aerosol delivery devices often include cartridges and aerosol delivery devices arranged with the longitudinal axes thereof being parallel to one another. However, as illustrated in FIGS. 2 and 3, the aerosol delivery device 100 of the present disclosure may be configured such that the longitudinal axis 104a of the electrical power source cavity 104 and the longitudinal axis 106a of the cartridge cavity 106 are non-coaxial.

Configuring the electrical power source cavity 104 and the cartridge cavity 106 with parallel, but non-coaxial, longitudinal axes 104a, 106a may provide numerous benefits. In this regard, the aerosol delivery device 100 may define a relatively shorter length due to the cartridge 200 and the electrical power source 300 being positioned beside one another, instead of in an end-to-end relationship. Further, by configuring the electrical power source cavity 104 and the cartridge cavity 106 beside one another, the aerosol delivery device 100 may define an overall shape that is more suitable for transport in a user's pocket. Additionally, this configuration may allow the aerosol delivery device 100 to more easily fit in a user's hand. In this regard, a user may more easily carry and use the aerosol delivery device in a concealed fashion within a palm of the user's hand due to the relatively shorter length thereof, which may be desirable in certain social settings.

The side-by-side configuration may also provide a relatively large internal volume within the housing 102 suitable for receipt of the components of the aerosol delivery device 100 in a number of various positions. By contrast, aerosol delivery devices arranged end-to-end have limited options with respect to the positions of components therein, due to the reservoir in the cartridge and the electrical power source in the control body typically defining cylindrical configurations. Thereby, any remaining space in the cartridge and the control body is typically annular or cylindrical in shape, which is not suitable for receipt of many components in a space efficient manner. Further, the relatively larger internal volume of the aerosol delivery device 100 of the present disclosure provided by the housing 102 may accommodate a relatively larger electrical power source 300 and/or a relatively larger cartridge 200, such that the respective electric and aerosol precursor composition storage capacities thereof may be increased. Additionally, the relatively large internal volume of the aerosol delivery device 100 may accommodate various commercially available electrical power sources, rather than just custom electrical power sources which may be required for cylindrical configurations, such that expenses associated with the components of the aerosol delivery device may be reduced.

The side-by-side configuration may additionally provide a relatively large exterior surface area. Further, the side-by-side configuration may provide relatively planar exterior surfaces (which may be slightly curved for ergonomic or aesthetic purposes), which may be more suitable for the display 116, as opposed to the sharply curved surfaces provided by a cylindrical aerosol delivery device. In this regard, commercially-available electronic displays typically define a planar display surface.

Thereby, for example, the electronic display 116 may be positioned at a number of locations and may define a relatively larger size than an electronic display on an aerosol delivery device defining a cylindrical configuration. In the illustrated embodiment the electronic display 116 is positioned at a top of the body portion 102a of the housing 102. The external opening 108 to the cartridge cavity 106 may also be positioned at the top of the body portion 102a of the housing. This position of the electronic display 116 may allow a user to view the electronic display while the aerosol delivery device is grasped in the user's hand in a manner suitable for taking a draw on the cartridge 200. In this regard, the user's hand may extend around the sides of the aerosol delivery device, such that the top surface of the aerosol delivery device, at which the electronic display 116 and the exposed portion of the cartridge 200 are positioned, is exposed and uncovered by the user's hand. Thus, various information regarding the aerosol delivery device 100 may be easily viewed during normal usage. For example, the data displayed by the electronic display 116 may include a remaining cartridge aerosol precursor composition level, a remaining power source level, historical usage information, heat and aerosol output settings, a charging status, a communication status (e.g., when linked to another device via Bluetooth or other communication protocol), the time, and/or various other data.

The side-by-side configuration of the aerosol delivery device 100 of the present disclosure may provide additional benefits. For example, the cartridge 200 may engage the control body 101 in a manner that may provide for a secure connection therebetween, which may reduce stress and strain thereon as compared to embodiments of aerosol delivery devices in which the connection between the cartridge and control body is exposed (e.g. in embodiments in which the cartridge and the control body are arranged end-to-end). In this regard, the coupler 114 may be recessed in or proximate the cartridge cavity 106 such that the housing 102 protects the connection between the cartridge 200 and the control body 101. Further, a portion, and more preferably a majority, of the longitudinal length of the cartridge 200 may be retained in the cartridge cavity 106 and the size and shape of the cartridge cavity may substantially correspond to that of the cartridge, such that the housing 102 may resist movement of the cartridge, rather than the coupler 114 bearing the entirety of such stress and strain associated with forces applied to one or both of the cartridge and the control body 101. In this regard, in aerosol delivery devices configured with a control body and a cartridge arranged end-to-end, the connection between the cartridge and the control body may bear all or substantially all of the stress and strain associated with force applied to one or both of the cartridge and the control body. Such stress and strain may damage the connection therebetween, which can impede operation thereof, due to the connection including an electrical connection that supplies current to the cartridge for vaporization purposes. Further, although "mod" devices may define configurations other than the end-to-end configuration described above, such devices often include exposed electrical connectors that are subject to stress and strain. Accordingly, the side-by side, parallel but non-coaxial configuration of the electric power source cavity 104 and the cartridge cavity 106 of the aerosol delivery device 100 of the present disclosure may provide various benefits.

Various embodiments of the cartridge 200 may be employed in the aerosol delivery device 100. In this regard, a side view of the cartridge 200, rather than a sectional view therethrough, is illustrated in FIG. 3 in light of the various possible configurations of the components of the cartridge. However, one example embodiment of the cartridge is illustrated in FIG. 4.

As illustrated in FIG. 4, the cartridge 200' may comprise a base shipping plug 202', a base 204', a control component terminal 206', an electronic control component 208', a flow director 210', an atomizer 212', a reservoir substrate 214', an outer body 216', a label 218', a mouthpiece 220', and a mouthpiece shipping plug 222' according to an example embodiment of the present disclosure. The base 204' may be coupled to a first end of the outer body 216' and the mouthpiece 220' may be coupled to an opposing second end of the outer body to at least partially enclose the remaining components of the cartridge 200' therein, with the exception of the label 218', the mouthpiece shipping plug 222', and the base shipping plug 202'. The base 204' may be configured to engage the coupler 114. In some embodiments the base 204' may comprise anti-rotation features that substantially prevent relative rotation between the cartridge and associated device including a power source as disclosed in U.S. Pat. App. Pub. No. 2014/0261495 to Novak et al., which is incorporated herein by reference in its entirety.

The base shipping plug 202' may be configured to engage and protect the base 204' prior to use of the cartridge 200'. Similarly, the mouthpiece shipping plug 222' may be configured to engage and protect the mouthpiece 220' prior to use of the cartridge 200'. The control component terminal 206', the electronic control component 208', the flow director 210', the atomizer 212', and the reservoir substrate 214' may be retained within the outer body 216'. The label 218' may at least partially surround the outer body 216' and include information such as a product identifier thereon.

The atomizer 212' may comprise a first heating terminal 234a' and a second heating terminal 234b', a liquid transport element 238', and a heating element 240'. In this regard, the reservoir substrate 214' may be configured to hold an aerosol precursor composition. The reservoir substrate 214' is in fluid connection with the liquid transport element 238' so as to transport the aerosol precursor composition from the reservoir substrate 214' to the heating element 240' (e.g., via capillary action). Thereby, when current is directed to the heating element 240' via the heating terminals 234a', 234b', the aerosol precursor composition may be vaporized.

Various other details with respect to the components that may be included in the cartridge 200', are provided, for example, in U.S. Pat. App. Pub. No. 2014/0261495 to Novak et al., which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow director, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 20 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 21 thereof illustrates a perspective view of a base with an anti-rotation mechanism; FIG. 22 thereof illustrates a perspective view of a coupler with an anti-rotation mechanism; and FIG. 23 thereof illustrates a sectional view through the base of FIG. 21 thereof and the coupler of FIG. 22 thereof in an engaged configuration.

In another embodiment the cartridge 200 may be substantially similar, or identical, to the cartridge disclosed in U.S. patent application Ser. No. 14/286,552 to Brinkley et al., filed May 23, 2014, which is incorporated herein by reference in its entirety. Thus, for example, the cartridge may include a flow director defining a non-tubular configuration, an electronics compartment sealed with respect to a reservoir compartment, and/or any of the various other features and components disclosed therein. Accordingly, it should be understood that the particular embodiments of the cartridge 200 described herein is provided for example purposes only.

In this regard, a sectional view through an additional embodiment of the cartridge 200 is illustrated in FIG. 5. As illustrated, the cartridge 200" may include a base 204", a control component terminal 206", an electronic control component 208", a flow director 210" which may be defined by an outer body 216" or a separate component, an atomizer 212", and a mouthpiece 220" according to an example embodiment of the present disclosure. The atomizer 212" may comprise a first heating terminal 234a" and a second heating terminal 234*b*", a liquid transport element 238" and a heating element 240". The cartridge 200" may additionally include a base shipping plug, a label, and a mouthpiece shipping plug, as described above.

The base 204" may be coupled to a first end of the outer body 216" and the mouthpiece 220" may be coupled to an opposing second end of the outer body to at least partially enclose the remaining components of the cartridge 200" therein. In some embodiments the base 204" may comprise anti-rotation features that substantially prevent relative rotation between the cartridge and associated device including a power source as disclosed in U.S. Pat. App. Pub. No. 2014/0261495 to Novak et al., which is incorporated herein by reference in its entirety.

The cartridge 200" may further comprise a sealing member 242" and an initial liquid transport element 244". In this regard, the outer body 216" and/or an additional component may be configured to hold an aerosol precursor composition 246" in a reservoir 248". In some embodiments the reservoir 248" may be configured to be refillable, whereas in other embodiments the cartridge 200" may be configured for a single use. The sealing member 242" may be positioned at an end of the chamber 248" and include one or more apertures 250" that allow the aerosol precursor composition 246" to contact the initial liquid transport element 244". Further, the liquid transport element 238" of the atomizer 212" may be in contact with the initial liquid transport element 244". Both the initial liquid transport element 244" and the liquid transport element 238" of the atomizer 212" may comprise wicking and/or porous materials that allow movement of the aerosol precursor composition 246" therethrough (e.g., via capillary action), such that the aerosol precursor composition may be drawn to the heating element 240" and heated and vaporized when current is applied to the heating element via the heating terminals 234*a*", 234*b*" by the controller 110 of the control body 101 (see, e.g., FIG. 6).

FIG. 6 illustrates the aerosol delivery device 100 when the electrical power source 300 is received in the electrical power source cavity 104, and the cartridge 200" of FIG. 5 is received in the cartridge cavity 106. As illustrated, in some embodiments, the electrical circuit may additionally include an illumination source 122 such as a light emitting diode (LED). Further, the control body 101 may include an illumination source cover 124, which may cover, protect, and/or conceal the illumination source 122. The illumination source cover 124 may be translucent or transparent such that light emitted by the illumination source may travel therethrough. In some embodiments the illumination source cover 124 may be tinted or diffuse such that the presence of the illumination source is hidden or obscured when not in use.

As further illustrated in FIG. 6, in some embodiments the cartridge 200" may include a viewing window 252", which may allow a user to view a quantity of the aerosol precursor composition 246" remaining in the reservoir 248". For example, all or a portion of the outer body 216" of the cartridge 200" may comprise a translucent or transparent material. The illumination source 122 and the illumination source cover 124 may be positioned in the body portion 102*a* of the housing 102 at the cartridge cavity 106 at a position that aligns with the viewing window 252" such that light produced by the illumination source may be directed into the cartridge 200" to facilitate viewing of the level of the aerosol precursor composition 246". In this regard, the body portion 102*a* of the housing 102 may include a cutout or other feature defining a viewing opening 126. Thereby, the user may be able to see the level of the aerosol precursor composition 246" through the viewing opening 126.

The controller 110 may direct the illumination source 122 to output light under certain circumstances, such as after a draw on the cartridge 200" is detected. The illumination source 122 may additionally or alternatively output light when a separate actuator (e.g., a button) is depressed or otherwise actuated. Accordingly, a user may be kept apprised of a level of the aerosol precursor composition in the cartridge 200".

Note that inclusion of the illumination source 122 is optional. In this regard, ambient light be sufficient for viewing the level of the aerosol precursor composition 246" through the viewing opening 126 in some embodiments. However, inclusion of the illumination source 122 may be preferable due to increased usability in low-light situations.

The controller 110 may be configured to control one or more operations of the aerosol delivery device 100. The controller 110 may verify that the cartridge 200 is authentic using information provided by the control component 208', 208". Usage of the cartridge 200 may be allowed only if the cartridge is determined to be authentic. Further, when a user draws on the cartridge 200, the flow sensor 118 (e.g. a pressure sensor) may detect the draw. In response, the controller 110 may direct current to the cartridge 200 such that the heating element 240', 240" produces heat and vaporizes the aerosol precursor composition, which may be directed to the user. In addition, the aerosol delivery device may include an actuator that may be manually actuated to trigger the controller to direct current to the cartridge 200. The actuator may be used in lieu of the flow sensor 118, or to provide supplemental power from the electrical power source to the cartridge to change (e.g., increase) the aerosol output of the aerosol delivery device. In other embodiments the actuator may be used in conjunction with the controller to adjust the amount of power directed from the electrical power source to the cartridge, such that the aerosol delivery device may have various aerosol output settings (e.g., aerosol mass output settings). Accordingly the actuator (e.g., a button or button assembly) may be configured to control a power output level directed from the electrical power source to the cartridge.

In some embodiments the actuator (e.g., button or button assembly) may have selective regions or a plurality of regions such as a lower region, a middle region, and an upper region. Each region of the actuator may be configured to direct a differing level of power (e.g., current and/or voltage) a from the electrical power source to the cartridge. Thereby, the differing regions of the actuator may each correspond to a differing aerosol output setting. The actuator may include one or a plurality of sensors (e.g., pressure and/or force sensors) at each region such that the force applied to the actuator by the user at one or more of the regions may be detected to control the output of the aerosol via differing selectable power output levels directed from the electrical power source to the cartridge. Accordingly, the power output level may be controlled based on a location at which the actuator is actuated. Alternatively or additionally, the power output level may be controlled based on the amount of force applied to the actuator, which may be determined via a force sensor (e.g., a stress or strain sensor).

As may be understood, the exact shape and dimensions of the aerosol delivery device 100 may vary. In this regard, FIGS. 7-10 illustrate an alternate embodiment of the control body 101', wherein only those differences with respect to the control body 101 described above are noted. Thus, each of the aerosol delivery devices may include some or all of the components and features described herein in any combination, unless otherwise noted.

As illustrated in FIG. 7, the control body 101' may define a more rounded profile for improved ergonomics. As further illustrated in FIG. 7, the control body 101' may further comprise an indicator 128'. The indicator 128' may output light to indicate an operational status of the control body. In some embodiments the indicator 128' may be used to communicate the operational status of the device without usage of the electronic display surface 116'. For instance, the indicator 128' may flash or change colors when the cartridge is low in aerosol precursor composition or to indicate the electrical power source needs recharging or replacement. In addition, the indicator 128' may light up when the flow sensor detects a puff on the cartridge.

In some embodiments the indicator 128' may be configured to illuminate with one or more of a plurality of colors, durations, frequencies, and/or intensities to indicate to the user certain conditions of the aerosol delivery device such as the power output level, the status of the electrical power source, and/or the activated or inactivated state of the aerosol delivery device which correspond to the output of the indicator. Thereby, the indicator 128' may include an illumination source that activates with one or more of a plurality of colors, durations, frequencies, and/or intensities to indicate to the user certain conditions of the aerosol delivery device such as the power output level, the status of the power source, and/or the activated or inactivated state of the aerosol delivery device. The indicator 128' may be configurable by the user to control the color or colors of the illumination source and/or other output parameters thereof. Further, the user may be able to control which device status value is communicated to the user by the illumination signal.

As additionally illustrated in FIG. 7, the body portion 102a' of the housing 102' may include a side opening 130'. The side opening 130' may be configured to engage an outer cover 132' (e.g., via interference fit), which is illustrated in FIG. 8. Thereby, the outer cover 132' may be engaged with an exterior of the housing 102'. In some embodiments the outer cover 132' may comprise silicon, which may provide enhanced grip such that it is easier to retain the control body 101' in the hand without dropping it. However, various other materials (e.g., other rubbers), which may be textured or smooth, may be employed in other embodiments. Use of a resilient outer cover 132' may provide various other benefits. For example, in one embodiment, depression of the outer cover 132' at the side opening 130' may trigger the illumination source 122 (e.g., via actuation of an actuator) to illuminate the fluid level in the cartridge 200. In another embodiment, the depression of the outer cover 132' at the side opening 130' may trigger the illumination source 122, where the duration of the depression of the outer cover corresponds to the duration of the activation of the illumination source, such that the user may continuously illuminate the cartridge 200 for a desired duration during filling or refilling of the cartridge or when otherwise desired for a user-selected period of time.

FIG. 9 illustrates a partial side view of the control body 101'. As illustrated, the illumination source cover 124' may be aligned with the viewing opening 126' as described above. In this illustrated embodiment, the viewing opening 126' may be relatively wide so as to facilitate viewing of the level of the aerosol precursor composition in the cartridge. For example, the viewing opening 126' may define an opening with a width perpendicular to the longitudinal axis 106a' of the cartridge cavity 106' that is equal to at least half of a diameter of the cartridge in some embodiments.

As noted above, in some embodiments the body portion of the housing of the control body may comprise multiple pieces. In this regard, FIG. 10 illustrates a first section 102a1' of the body portion 102a' of the housing 102' (see, FIG. 7). A second section 102a2' and a third section 102a3' of the body portion 102a' of the housing 102' are illustrated in FIG. 7. The third section 102a3' may be integral with the section 102a2', or a separate component. The first and second sections 102a1', 102a2' of the body portion 102' of the housing 102' may be configured to engage the access door 102b' (see, FIG. 10). The electronic display 116' may be positioned at (e.g., under) the third section 102a3' of the body portion 102a' of the housing 102'. In this regard, all or a portion of the housing 102' may be translucent or transparent in some embodiments. The housing 102' may additionally include an illumination source or have an illumination source in proximity thereto. For example, the housing 102' may include the illumination source 122 described above, which may be configured to emit direct or indirect illumination through the housing 102' where the housing may be translucent or transparent.

As illustrated in FIG. 10, the first section 102a1' of the body portion 102a' of the housing 102' may additionally include a side opening 134' configured to engage the outer cover 132' (see, e.g., FIG. 8). Thereby, the outer cover 132' may be firmly held in place via the opposing side openings 130', 134'. Whereas the outer body 132' may provide enhanced grip, the third section 102a' may comprise a metal such as aluminum for enhanced strength and/or improved cosmetic appearance, or a separate outer body defining such characteristics may be attached to the third section.

FIG. 10 further illustrates an inside of the first section 102a1' of the body portion 102a' of the housing 102'. As illustrated, the housing 102' may define one or more ribs 136', which may be configured to retain the electric power source 300 (see, e.g., FIG. 3) within the electrical power source cavity 104' and/or retain the cartridge 200 (see, e.g., FIG. 3) in the cartridge cavity 106'. In this regard, the ribs 136' may be curved or otherwise tailored to match the size and shape of the electric power source 300 and/or the cartridge 200. The ribs 136' may extend to an end portion 138'. The end portions 138' of the ribs 136' at the first section 102a1' of the body portion 102a' of the housing 102' may be configured to engage corresponding end portions of the ribs at the second section 102a2' (see, FIG. 7) of the body portion of the housing so as to separate the electrical power source cavity 104' from the cartridge cavity 106' to retain the electrical power source 300 and the cartridge 200 (see, FIG. 3) respectively therein. In this regard, the end portions 138' of the ribs 136' may collectively define a divider wall 107' that is segmented along the length thereof. Usage of the ribs 136', rather than a solid structure, may reduce the quantity of material required to form the housing 102', thereby additionally reducing the weight of the housing while still retaining the components of the control body 101' in the desired positions and providing added stiffness. The ribs 136' may comprise a non-rigid material such as foam or a thermoplastic polymer or include an element comprising foam, thermoplastic polymer, or other non-rigid material that allows the ribs 136' to compress or displace in the event that the electrical power source 300 undergoes changes in diameter such that can occur with diametric swelling that is common with lithium-type batteries. In this regard, the ribs 136' may at least partially surround the electrical power source 300 (see, e.g., FIG. 3).

As additionally illustrated in FIG. 10, the first section 102a1' of the body portion 102a' of the housing 102' may include protrusions and/or receptacles 140', which may be configured to engage corresponding receptacles/protrusions at the second section 102a2' (see, FIG. 7). Thereby, the sections 102a1', 102a2' of the housing 102' may interlock with one another when assembled.

As illustrated in FIG. 10, section 102b' may include an orifice 137' or plurality of orifices in fluid communication with the electrical power source cavity 104' and the atmosphere outside of the housing 102' to allow for the escape of any gas or gases that may be produced by the electrical power source 300 (see, e.g., FIG. 3) to prevent the gas or gases from generating a region of increased pressure within the housing 102'. The orifice 137' may comprise one or more openings of sufficient cross sectional area as to prevent a pressure differential between the internal region of the housing 102' and the outside atmosphere. In one embodiment the orifice 137' may include a permeable membrane or porous material that allows gas or gases that may be produced by the electrical power source 300 (see, e.g., FIG. 3) to escape to the outside atmosphere while preventing the entrance of liquid into the housing 102' due to the selective permeability of the membrane or porous material.

FIGS. 11-15 illustrate an additional embodiment of the control body 101". The control body 101" may be substantially similar to the control body 101' of FIGS. 7-10 in one or more respects. In this regard, as illustrated in FIGS. 11 and 12, the control body 101" may include a housing 102" comprising a body portion 102a" and an access door 102b" which may be secured to the body portion via a screw 120" (see, FIG. 13). The body portion 102a" may include multiple sections including first and second sections 102a1", 102a2". The first section 102a1" may define protrusions and/or receptacles 140" configured to engage corresponding receptacles/protrusions at the second section 102a2' (see, FIG. 7). The body portion 102a" may define one or more ribs 136" that respectively extend to an end portion 138" to define a dividing wall 107". As illustrated the ribs 136" may extend in both the power source cavity 104" and the cartridge cavity 106" in some embodiments to thereby assist in respectively retaining the electrical power source and the cartridge therein. Further, the control body 101" may include the indicator 128" and an outer cover 132" (see, FIG. 14). The electronic display 116" may be positioned at the top of the housing 102" proximate the opening to the external opening 108" to the cartridge cavity 106", which extends along the longitudinal axis 106a".

However, the control body 101" may differ in one or more respects from the control bodies described above. In this regard, in addition to the end portions 138" of the ribs 136", the dividing wall 107" may additionally include a partial wall 109", which further assists in retaining a cartridge in the cartridge cavity 106". Further, as illustrated in FIGS. 11 and 12, in some embodiments the body portion 102a" of the housing 102" may include first and second side openings 130a", 130b" at the first section 102a1" and first and second side openings 134a", 134b" at the second section 102a2" thereof (see, FIGS. 11 and 13). Usage of multiple side openings 130a", 130b", 134a", 134b" at each section 102a1", 102a2" of the body portion 102a" of the housing 102" may provide for improved engagement of the outer cover 132" therewith, as illustrated in FIG. 12.

Further, as illustrated in FIG. 15, and as noted above, in some embodiments the viewing opening 126' may be relatively wide (see e.g., FIG. 9). However, as illustrated in FIG. 13, in other embodiments the viewing opening 126" may be relatively less wide. For example, the viewing opening may define a width that is equal to less than half of a diameter of the configured to be received in the cartridge compartment 106" in some embodiments. Whereas a wide viewing opening may facilitate viewing of the level of the aerosol precursor composition, a relatively less wide viewing opening may provide more protection to the cartridge, while still allowing a user to view the level of the aerosol precursor composition.

In an additional embodiment, FIG. 16 illustrates a method for assembling an aerosol delivery. As illustrated, the method may include providing a housing at operation 402. The housing may define an electrical power source cavity configured to receive an electrical power source and a cartridge cavity configured to receive a cartridge including an aerosol precursor composition. The electrical power source cavity and the cartridge cavity may be elongated and respectively define a longitudinal axis. The longitudinal axis of the electrical power source cavity and the longitudinal axis of the cartridge cavity may be non-coaxial and oriented substantially parallel to one another. Further, the method may include positioning an electrical contact in the electrical power source cavity, the electrical contact being configured to engage the electrical power source at operation 404. Additionally, the method may include positioning a coupler in the cartridge cavity, the coupler being configured to engage the cartridge at operation 406.

In some embodiments the method may further comprise inserting the electrical power source in the electrical power source cavity and engaging the electrical power source with the electrical contact. The method may additionally include inserting the cartridge into the cartridge cavity and engaging the cartridge with the coupler. Inserting the cartridge into the cartridge cavity may include inserting the cartridge through an external opening defined by the housing.

Providing the housing at operating 402 may include defining a viewing opening at the cartridge cavity. Further, the method may include engaging an outer cover with an exterior of the housing. The method may additionally include positioning an illumination source in the housing. The illumination source may be configured to illuminate the cartridge in the cartridge cavity. The method may further include engaging an electronic display with the housing. Providing the housing at operation 402 may include engaging a first body portion with a second body portion. Providing the housing at operation 402 may further include engaging an access door with at least one of the first body portion and the second body portion, the access door being configured to selectively provide access to the electrical power source cavity.

An additional embodiment of an aerosol delivery device 500 is illustrated in FIG. 17. As illustrated the aerosol delivery device 500 may include a control body 501 and a cartridge. In the illustrated embodiment the cartridge 200" from FIG. 5 is included in the aerosol delivery device 500. However, as may be understood, other cartridges may be employed in other embodiments.

The control body 501 may include a housing 502. The housing 502 may be integral or comprise a plurality of pieces. For example, the housing 502 may include an electrical power source portion 502a, an access door 502b, and a coupler portion 502c. Access door 502b may include an orifice or plurality of orifices in fluid communication with the atmosphere outside of the housing 502b to allow for the escape of any gas or gases that may be produced by electrical power source 504 (see, FIG. 18) to prevent the gas or gases from generating a region of increased pressure within the housing 502 as described above with respect to the orifice 137 in FIG. 10. In this regard, each of the housings of the aerosol delivery devices of the present disclosure may include such an orifice. The orifice may preferably be located at an access door to conceal the orifice and position the orifice at the electrical power source cavity, but the orifice may be located at other positions in other embodiments.

In this regard, FIG. 18 illustrates a partial exploded view of the control body 501. As illustrated, the electrical power source portion 502a of the housing 502 may include a first body portion 502a1 and a second body portion 502a2. The first body portion 502a1 and the second body portion 502a2 may be configured to engage one another and define an electrical power source cavity 504. The electrical power source cavity 504 may be configured to receive an electrical power source 600 (e.g., a battery and/or a capacitor). The electrical power source cavity 504 may define a first longitudinal axis 504a.

Further, the coupler portion 502c of the housing 502 may be configured to engage the electrical power source portion 502a of the housing. A coupler 514 may be engaged with the coupler portion 502c of the housing 502. For example, the coupler 514 may be positioned at least partially within the coupler portion 502c of the housing 502.

The coupler 514 may be configured to engage the cartridge 200" (see, FIG. 17), which may include an aerosol precursor composition. When engaged with the coupler 514, the cartridge 200" may extend along a second longitudinal axis 200a", as illustrated in FIG. 17. The first longitudinal axis 504a, which is defined by the electrical power source cavity 504, and the second longitudinal axis 200a", which is defined by the cartridge 200", may be non-coaxial and oriented substantially parallel to one another. This configuration may provide various benefits as noted above with respect to embodiments of control bodies wherein the longitudinal axis of the electrical power source cavity and the longitudinal axis of the cartridge cavity are non-coaxial but substantially parallel.

In some embodiments the cartridge 200" may be at least partially received in a coupler cavity 506 defined by the coupler portion 502c of the housing 502. In this regard, as noted above, the coupler 514 may be at least partially received in the coupler cavity 506. Thereby, a depth of the coupler cavity 506 as well as the position of the coupler 514 (see, FIG. 18) therein may determine whether or not the cartridge 200" is at least partially received in the coupler cavity 506. Partially receiving the cartridge 200" in the coupler cavity 506 may provide for improved engagement of the cartridge with the control body 501 and/or reduce the susceptibility of damage or contamination to the coupler 514. However, in other embodiments the cartridge 200" may not extend into the coupler portion 502c of the housing 502. This configuration may facilitate engagement of the cartridge 200" with the coupler 514 and allow for usage of a wider variety of shapes and sizes of cartridges with the control body 501.

The control body 501 may additionally include a controller 510 (see, e.g., FIG. 20), which is not shown in FIG. 18 for clarity purposes. The controller 510 may comprise a control board in some embodiments. The controller 510 may be configured to control some or all of the functions of the control body 501 including directing current from the electrical power source 600 to the cartridge 200". In this regard, the controller 510 may be electrically coupled to the electrical power source 600.

As illustrated in FIG. 18, the control body 501 may additionally include one or more button assemblies. In particular, the control body 501 may include a first button assembly 542 and second button assembly 544. As illustrated in FIG. 19, the first button assembly 542 may be configured to actuate a first switch 546 on the controller 510. Similarly, the second button assembly 544 may be configured to actuate a second switch 548 on the controller 510. In this regard, the button assemblies 542, 544 may be configured to bend or otherwise move to actuate the switches 546, 548. By way of example, the first button assembly 542 and the second button assembly 544 may be hingedly coupled to one or both of the first body portion 502a1 and the second body portion 502a2 (see, e.g., FIG. 18) of the electrical power source portion 502a of the housing 502.

Thereby, actuation of the switches 546, 548 may control one or more functions of the control body 501. For example, actuation of the first switch 546 may direct current from the electrical power source 600 to the cartridge 200" (see, FIG. 17) to heat an aerosol precursor composition therein and produce an aerosol. Further, actuation of the second switch 548 may control other functions.

By way of example, the control body 501 may further comprise an illumination source 522 such as a light emitting diode (LED). The illumination source 522 may be configured to output illumination. In this regard, the control body 501 may include an illumination source cover 524, which may cover, protect, and/or conceal the illumination source 522. The illumination source cover 524 may be translucent or transparent such that light emitted by the illumination source may travel therethrough. In some embodiments the illumination source cover 524 may be tinted or diffuse such that the presence of the illumination source 522 is hidden or obscured when not in use.

The illumination source 522 may be configured to illuminate the cartridge 200". In particular, as schematically illustrated in FIG. 17, the cartridge 200" may include the viewing window 252" such that a level of the aerosol precursor therein may be viewed as described above. Accordingly, the second button assembly 544 may be employed to turn on the illumination source 522 such that illumination is directed through the viewing window 252" of the cartridge 200" and thereby a user may more easily view a level of aerosol precursor composition therein, and/or the second switch may perform other functions. For example, in another embodiment depression of the second button assembly 544, and thereby actuation of the second switch 548, may cause the controller 510 to provide supplemental power from the electrical power source to the cartridge to increase the aerosol output of the aerosol delivery device, or to direct power to the cartridge, regardless of whether a draw on the cartridge is detected. In this regard, in some embodiments the aerosol delivery device may not include a flow sensor. In other embodiments the second button assembly 544 may be used to actuate the second switch 548 to cycle through various adjustable controller power levels, such that the device may have various aerosol mass output settings, or various other functions may be controlled. Accordingly, the second button assembly 544 and/or any of the other actuators discussed herein may be configured to control a power output level directed from the electrical power source to the cartridge and/or otherwise control a quantity (e.g., mass) of aerosol outputted.

In some embodiments the second button assembly 544 may at least partially define a dividing wall 550 that separates the cartridge 200" from the electrical power source cavity 504 (see, FIG. 18). Further, as described below, the controller 510 may be received in the electrical power source cavity 504. Thereby, the second button assembly 544 may include the illumination source cover 524 at the dividing wall 550 such that the illumination may be directed therethrough to the cartridge 200".

Assembly of the control body 501 may be performed in various manners. In one embodiment the controller 510 may be at least partially wrapped about the electrical power source 600, as illustrated in FIG. 20. For example, the controller 510 may be bent or configured such that the power source 600 is received between opposing substantially parallel walls of the controller. The controller 510 may be electrically connected to the electrical power source 600 at this time as well. In this regard, by way of example, the electrical power source may include wires or other electrical leads that are soldered or otherwise connected to the controller 510.

As illustrated in FIG. 21, the controller 510 and the electrical power source 600 may be inserted into the housing 502. More particularly, the controller 510 and the electrical power source may be received in the electrical power source cavity 504. In some embodiments the housing 500 may include features configured to engage the controller 510. For example, as illustrated, the controller 510 may be received in a slot 552 which may be defined by an extension 554 formed by the first body portion 502a1 of the electrical power source portion 502a of the housing 502. Thereby, the extension 554 may support the controller 510 to allow for actuation of the switches 546, 548 in the manner described above.

In one embodiment the first button assembly 542 may be engaged with the first body portion 502a1 of the electrical power source portion 502a of the housing 502 before the controller 510 and the electrical power source 600 are inserted into the electrical power source cavity 504. For example, a portion of the first button assembly 542 may be welded (e.g., ultrasonic welded), adhered, engaged via interference fit, or mechanically coupled to the first body portion 502a1 of the electrical power source portion 502a of the housing 502. Thereby, the first button assembly 542 may be engaged with the first body portion 502a1, but still able to move to actuate the first switch 546 as described above. Additionally, as further illustrated in FIG. 21, in some embodiments the second button assembly 544 may be engaged with the first body portion 502a1 of the electrical power source portion 502a of the housing 502 before the controller 510 and the electrical power source 600 are inserted into the electrical power source cavity 504. For example, a portion of the second button assembly 544 may be welded (e.g., ultrasonic welded), adhered, engaged via interference fit, or mechanically coupled to the first body portion 502a1 of the electrical power source portion 502a of the housing 502. Thereby, the second button assembly 544 may be engaged with the first body portion 502a1, but still able to move to actuate the second switch 546 as described above.

Returning to FIG. 20, the controller 510 may include a connector 556. The connector 556 may comprise an electrical connector and/or a data connector. Thereby, the connector 556 may be employed to recharge the electrical power source 600 and/or transmit data to or from the controller 510. As illustrated in FIG. 21, the housing 502 may include a recess 558 configured to receive the connector 556. For example, the recess 558 may be defined by one or both of the first body portion 502a1 and the second body portion 502a2 of the electrical power source portion 502a of the housing 502.

As illustrated in FIG. 22, the second body portion 502a2 of the electrical power source portion 502a of the housing 502 may be engaged with the first body portion 502a1 after the controller 510 and the electrical power source 600 are inserted into the electrical power source cavity 504. For example, the second body portion 502a2 may be welded (e.g., ultrasonic welded), adhered, engaged via interference fit, or mechanically coupled to the first body portion 502a1 of the electrical power source portion 502a of the housing 502. Further, the coupler portion 502c of the housing 502 may be engaged with the electrical power source portion 502a of the housing 502. For example, the coupler portion 502c may be welded (e.g., ultrasonic welded), adhered, engaged via interference fit, or mechanically coupled to the electrical power source portion 502a of the housing 502.

FIG. 22 further illustrates the coupler 514 engaged with the housing 502. In particular, the coupler 514 may be received in the coupler cavity 506. As illustrated in FIG. 23, additional components may be inserted in the coupler cavity 506. In particular, a seal 560 may be inserted through the coupler 514. Further, an electrical contact 562 may extend through the seal 560. The seal 560 may be configured to electrically insulate the coupler 514 from the electrical contact 562. In this regard, the electrical contact 562 may comprise a conductive material such as brass, and the seal 560 may comprising an electrically insulating material such as silicone. The electrical contact 562 may be engaged with a first terminal 564 (see, e.g., FIG. 22) of the controller 510. For example, the electrical contact 562 may be welded to the first terminal 564 after the first terminal is bent into contact therewith.

Further, a tab 566 may be engaged with the coupler 514 and received in the coupler cavity 506 defined by the coupler portion 502c of the housing 502. A fastener 568 (e.g., a nut) may be secured to the coupler 514 in order to retain the tab 566 in engagement therewith. The tab 566 may be coupled to a second terminal 570 (see, e.g., FIG. 22) of the controller 510. For example, the second terminal 570 may be welded to the tab 566 after the second terminal is bent into engagement therewith. Thereby, the coupler 514 may be electrically coupled to the controller 510. In another embodiment the second terminal 570 may directly engage the coupler 514. Regardless, positive and negative connections may be established with the cartridge 200" (see, e.g., FIG. 17) when the cartridge is engaged with the control body 501 via the electrical contact 562 and the coupler 514. Thereby, current may be directed to the cartridge 200" in order to vaporize the aerosol precursor composition therein as directed by the controller 510 when a user depresses the first button assembly 542 (see, e.g., FIG. 18).

After the various components noted above are inserted into the coupler cavity 506, the access door 502b (see, FIG. 18) may be engaged with the electrical power source portion 502a and the coupler portion 502c of the housing 502. Thereby, the control body 501 may define the completed configuration illustrated in FIG. 17.

Note that although the control bodies of the present disclosure are described herein as being usable with cartridges, it should be understood that the term "cartridge" is intended to include embodiments thereof referred to as "tanks" or "tank-style cartridges." Tanks are distinguishable from other embodiments of cartridges for aerosol delivery devices in that they may not include a reservoir substrate, at least a portion thereof may be transparent or translucent such that a level of aerosol precursor composition may be viewed, and the quantity of the aerosol precursor composition that may be received therein may be relatively large. Embodiments of tank-style cartridges are described in U.S. patent application Ser. No. 14/802,667, filed Jul. 17, 2015, to O'Brien, which is incorporated herein by reference in its entirety.

In an additional embodiment a method for assembling an aerosol delivery device is provided. As illustrated in FIG. 24, the method may include providing a housing defining an electrical power source cavity configured to receive an electrical power source, the electrical power source cavity defining a first longitudinal axis at operation 702. Further, the method may include engaging a coupler configured to engage a cartridge including an aerosol precursor composition with the housing such that the cartridge extends along a second longitudinal axis, the first longitudinal axis and the second longitudinal axis being non-coaxial and oriented substantially parallel to one another at operation 704. Additionally, the method may include positioning a controller in the housing, the controller being configured to engage the electrical power source at operation 706.

In some embodiments the method may further comprise engaging the electrical power source with the controller. Additionally, the method may include inserting the electrical power source in the electrical power source cavity simultaneously with positioning the controller in the housing at operation 706. Further, the method may include engaging the cartridge with the coupler. The cartridge may include a viewing window. The method may additionally include positioning an illumination source in the housing, the illumination source being configured to direct illumination through the viewing window.

In some embodiments providing the housing at operation 702 may include engaging a first body portion with a second body portion. Providing the housing at operation 702 may further include engaging an access door with at least one of the first body portion and the second body portion, the access door being configured to block access to the electrical power source cavity. Providing the housing at operation 702 may additionally include engaging a button assembly with at least one of the first body portion and the second body portion. Further, the method may include positioning an illumination source in the housing and engaging an illumination source cover with the button assembly, the illumination source cover being configured to direct illumination produced by the illumination source therethrough.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
a housing defining an electrical power source cavity configured to receive an electrical power source, the electrical power source cavity defining a first longitudinal axis; and
a coupler engaged with the housing and configured to engage a cartridge including an aerosol precursor composition such that the cartridge extends along a second longitudinal axis,
the first longitudinal axis and the second longitudinal axis being non-coaxial and oriented substantially parallel to one another,
wherein the housing comprises a button assembly that at least partially defines a dividing wall that separates the cartridge from the electrical power source cavity.

2. The aerosol delivery device of claim 1, further comprising the electrical power source.

3. The aerosol delivery device of claim 2, further comprising a controller, wherein the controller is wrapped at least partially about the electrical power source.

4. The aerosol delivery device of claim 1, further comprising the cartridge.

5. The aerosol delivery device of claim 4, wherein the cartridge comprises a viewing window.

6. The aerosol delivery device of claim 5, further comprising an illumination source configured to direct illumination through the viewing window.

7. The aerosol delivery device of claim 1, wherein the housing comprises a coupler portion, the coupler being positioned at least partially within the coupler portion.

8. The aerosol delivery device of claim 1, wherein the button assembly is configured to control a power output level directed from the electrical power source to the cartridge.

9. The aerosol delivery device of claim 1, further comprising an illumination source, wherein the button assembly includes an illumination source cover configured to direct illumination produced by the illumination source therethrough.

10. A method for assembling an aerosol delivery device, the method comprising:
providing a housing defining an electrical power source cavity configured to receive an electrical power source, the electrical power source cavity defining a first longitudinal axis, the housing comprising a button assembly at least partially defining a dividing wall that separates a cartridge including an aerosol precursor composition from the electrical power source cavity; and
engaging a coupler configured to engage the cartridge with the housing such that the cartridge extends along a second longitudinal axis,
the first longitudinal axis and the second longitudinal axis being non-coaxial and oriented substantially parallel to one another; and
positioning a controller in the housing, the controller being configured to engage the electrical power source.

11. The method of claim 10, further comprising engaging the electrical power source with the controller.

12. The method of claim 11, further comprising inserting the electrical power source in the electrical power source cavity simultaneously with positioning the controller in the housing.

13. The method of claim 10, further comprising engaging the cartridge with the coupler.

14. The method of claim 13, wherein the cartridge comprises a viewing window.

15. The method of claim 14, further comprising positioning an illumination source in the housing, the illumination source being configured to direct illumination through the viewing window.

16. The method of claim 10, wherein providing the housing comprises engaging a first body portion with a second body portion.

17. The method of claim 16, wherein providing the housing further comprises engaging an access door with at least one of the first body portion and the second body portion, the access door being configured to block access to the electrical power source cavity.

18. The method of claim 16, wherein providing the housing further comprises engaging the button assembly with at least one of the first body portion and the second body portion.

19. The method of claim 18, further comprising positioning an illumination source in the housing and engaging an illumination source cover with the button assembly, the illumination source cover being configured to direct illumination produced by the illumination source therethrough.

* * * * *